(12) United States Patent
Davis et al.

(10) Patent No.: US 7,718,442 B2
(45) Date of Patent: May 18, 2010

(54) SEALED SAMPLE STORAGE ELEMENT SYSTEM AND METHOD

(75) Inventors: James C. Davis, Carlsbad, CA (US); Mitchell D. Eggers, Carlsbad, CA (US); John W. Sadler, Belmont, CA (US)

(73) Assignee: GenVault Corporation, Carlsbad, CA (US)

( * ) Notice: Subject to any disclaimer, the term of this patent is extended or adjusted under 35 U.S.C. 154(b) by 845 days.

(21) Appl. No.: 10/302,647

(22) Filed: Nov. 22, 2002

(65) Prior Publication Data

US 2004/0101966 A1  May 27, 2004

(51) Int. Cl.
G01N 1/00 (2006.01)
(52) U.S. Cl. .................. 436/174; 436/176; 436/178; 422/99; 422/102
(58) Field of Classification Search .................. 42/68.1, 42/82.05, 82.06, 82.08, 99, 102, 104; 436/55, 436/56, 164, 174, 176, 179, 178
See application file for complete search history.

(56) References Cited

U.S. PATENT DOCUMENTS

| | | | | |
|---|---|---|---|---|
| 4,292,920 A | * | 10/1981 | Smith et al. | 118/425 |
| 4,643,879 A | | 2/1987 | Hanaway | |
| 4,684,613 A | | 8/1987 | Barrere | 435/301 |
| 4,767,716 A | | 8/1988 | Sakamaki et al. | |
| 4,824,641 A | | 4/1989 | Williams | |
| 4,896,024 A | | 1/1990 | Morello | 235/381 |
| 5,011,779 A | * | 4/1991 | Maimon | 435/309.1 |
| 5,096,676 A | | 3/1992 | McPherson et al. | |
| 5,120,662 A | | 6/1992 | Chan et al. | |

(Continued)

FOREIGN PATENT DOCUMENTS

JP 10-78388 3/1998

(Continued)

OTHER PUBLICATIONS

Elliot, J.C., Bowen, K.L., Walker, T., Sauve, V.M., and Fourney, R.M.: "Extration of DNA from FTA Blood Stain Collection Cards for Construction of a Large STR National DNA Data Base;" 8th International Symposium on Human ID, 1997.

(Continued)

*Primary Examiner*—Jill Warden
*Assistant Examiner*—Dwayne K Handy
(74) *Attorney, Agent, or Firm*—Cooley Godward Kronish LLP

(57) ABSTRACT

A system and method operative in accordance with the present disclosure facilitate storage and retrieval of individual or discrete samples of biological, non-biological, and chemical material stored on dry media. Sample material may be disposed upon or within a porous or solid (i.e., non-porous) sample storage medium and subsequently archived in, and retrieved from, storage elements such as multi-well plates, for example, using robotic devices or other automated apparatus. The disclosed system and method enable ejection of sample material from a sealed storage element into a specific well of a multi-well daughter plate, or into a specific cuvette, test tube, or similar container. In some embodiments, a sample carrier comprising a storage medium may be punched or ejected through a first seal of the storage element with an apparatus or implement such as a disposable piercing tip, for instance, inserted through a second seal of the storage element.

20 Claims, 12 Drawing Sheets

U.S. PATENT DOCUMENTS

| | | | |
|---|---|---|---|
| 5,125,240 A | 6/1992 | Knippscheer | 62/266 |
| 5,139,744 A | 8/1992 | Kowalski | 422/67 |
| 5,355,304 A | 10/1994 | DeMoranville | 364/413.02 |
| 5,366,896 A | 11/1994 | Margrey | 436/48 |
| 5,411,065 A | 5/1995 | Meador et al. | |
| 5,411,893 A | 5/1995 | Eden | 436/165 |
| 5,424,036 A | 6/1995 | Ushikubo | |
| 5,441,698 A | 8/1995 | Norell | 422/58 |
| 5,445,294 A | 8/1995 | Gardner | 221/1 |
| 5,460,057 A | 10/1995 | Ostrup | 73/864.81 |
| 5,638,170 A | 6/1997 | Trinka | |
| 5,736,332 A | 4/1998 | Mandecki | |
| 5,800,777 A | 9/1998 | Jehan | 422/63 |
| 5,800,785 A * | 9/1998 | Bochner | 422/101 |
| 5,805,456 A | 9/1998 | Higham | 364/479.06 |
| 5,841,975 A | 11/1998 | Layne | 395/200.33 |
| 5,853,666 A * | 12/1998 | Seaton et al. | 422/65 |
| 5,916,812 A * | 6/1999 | Chen et al. | 436/18 |
| 5,922,617 A | 7/1999 | Wang et al. | |
| 5,981,166 A * | 11/1999 | Mandecki | 435/4 |
| 5,984,116 A | 11/1999 | Babbs | |
| 5,985,214 A | 11/1999 | Stylli et al. | |
| 5,985,217 A | 11/1999 | Krulevitch et al. | |
| 6,007,779 A | 12/1999 | Lemieux et al. | |
| 6,086,824 A * | 7/2000 | Fanning et al. | 422/65 |
| 6,098,819 A | 8/2000 | Link | |
| 6,103,518 A | 8/2000 | Leighton | 435/286.3 |
| 6,108,588 A | 8/2000 | McGrady | 700/231 |
| 6,110,748 A * | 8/2000 | Reber et al. | 436/518 |
| 6,132,685 A * | 10/2000 | Kercso et al. | 422/104 |
| 6,156,565 A * | 12/2000 | Maes et al. | 435/287.3 |
| 6,159,425 A | 12/2000 | Edwards et al. | |
| 6,182,719 B1 | 2/2001 | Yahiro | |
| 6,245,295 B1 * | 6/2001 | Chen et al. | 422/48 |
| 6,251,343 B1 | 6/2001 | Dubrow et al. | |
| 6,265,219 B1 | 6/2001 | Giger et al. | |
| 6,274,374 B1 | 8/2001 | Astle | |
| 6,294,203 B1 | 9/2001 | Burgoyne | |
| 6,325,114 B1 | 12/2001 | Bevirt et al. | |
| 6,358,470 B1 | 3/2002 | Higuchi | |
| 6,372,185 B1 | 4/2002 | Shumate et al. | |
| 6,395,231 B1 | 5/2002 | Kraemer et al. | |
| 6,402,837 B1 | 6/2002 | Shtrahman et al. | |
| 6,416,719 B1 | 7/2002 | Fawcett et al. | |
| 6,464,942 B2 | 10/2002 | Coffman et al. | |
| 6,485,690 B1 | 11/2002 | Pfost et al. | |
| 6,485,978 B1 | 11/2002 | Kirckoff et al. | |
| 6,508,984 B1 | 1/2003 | Turner et al. | |
| 6,518,060 B2 | 2/2003 | Heimberg et al. | |
| 6,534,015 B1 | 3/2003 | Viot et al. | |
| 6,556,923 B2 | 4/2003 | Gallagher et al. | |
| 6,649,403 B1 | 11/2003 | McDevitt et al. | |
| 6,652,724 B2 | 11/2003 | Michael et al. | |
| 6,678,577 B1 | 1/2004 | Stylli et al. | |
| 6,686,158 B2 | 2/2004 | Mandecki | |
| 6,752,967 B2 | 6/2004 | Farina et al. | |
| 6,767,748 B2 | 7/2004 | Yokokawa et al. | |
| 6,811,752 B2 * | 11/2004 | Barbera-Guillem | 422/100 |
| 6,943,035 B1 * | 9/2005 | Davies et al. | 436/180 |

FOREIGN PATENT DOCUMENTS

| | | |
|---|---|---|
| JP | 2002-125656 | 5/2002 |
| WO | 94/11388 A1 | 5/1994 |
| WO | 96/11406 A1 | 4/1996 |
| WO | 98/29736 A1 | 7/1998 |
| WO | 99/34214 A1 | 8/1999 |
| WO | 99/44062 A1 | 9/1999 |
| WO | 01/12327 A1 | 2/2001 |
| WO | WO 01/31317 | 5/2001 |
| WO | WO 01/31333 | 5/2001 |
| WO | 01/42796 A1 | 6/2001 |
| WO | 01/86410 A1 | 12/2001 |
| WO | 02/30561 A2 | 4/2002 |

OTHER PUBLICATIONS

Bever, R., Jarvis, D., DiPerro, D., and McElfresh K.; "Implementation of Laboratory Automation for the Analysis of STR Loci;" 8th International Symposium on Human ID, 1997.

Belgrader, P., and Marino, M.A.; Coupled DNA Purification and PCR Amplification of STR Loc i from Bloodstain Cards Using a Robotic System; BioTechniques, 19:427-432, 1995.

Hansen, P., and Blakesley R.: "Sample Archiving of Bacterial and Plasmid DNAs for Future Use;" Focus, vol. 20, No. 3, pp. 72-74, 1998.

* cited by examiner

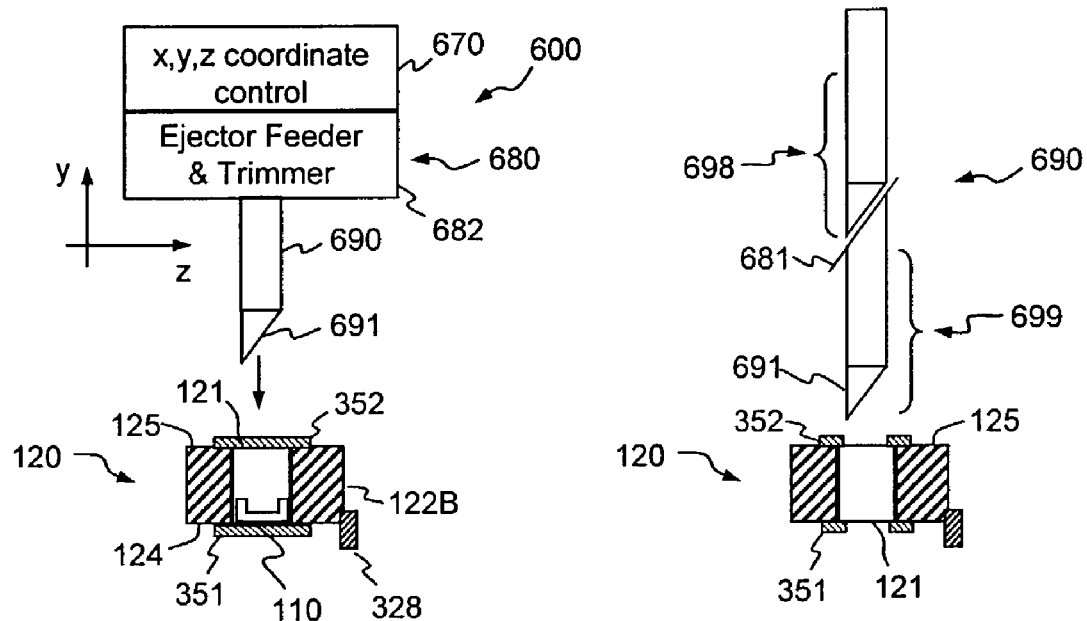
FIG. 6A
FIG. 6C
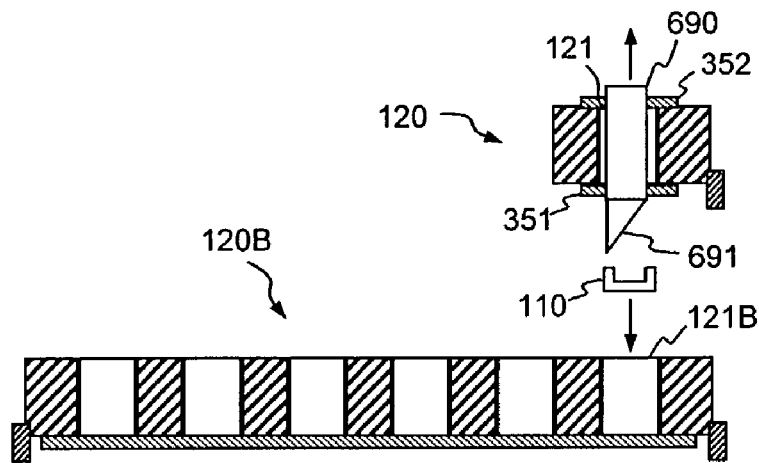
FIG. 6B

SEALED SAMPLE STORAGE ELEMENT SYSTEM AND METHOD

The present application is related to the following non-provisional applications: Ser. No. 10/252,352, filed Sep. 20, 2002, entitled "SYSTEM AND METHOD OF STORING AND RETRIEVING STORAGE ELEMENTS;" Ser. No. 10/150,770, filed May 17, 2002, entitled "SAMPLE CARRIER RECEIVER;" Ser. No. 10/150,771, filed May 17, 2002, entitled "SAMPLE CARRIER SYSTEM;" Ser. No. 10/005, 529, filed Nov. 7, 2001, entitled "APPARATUS, SYSTEM, AND METHOD OF ARCHIVAL AND RETRIEVAL OF SAMPLES;" Ser. No. 10/005,415, filed Nov. 7, 2001, entitled "ARCHIVE AND ANALYSIS SYSTEM AND METHOD;" and Ser. No. 10/007,355, filed Nov. 7, 2001, entitled "SAMPLE CARRIER." The disclosures of all the foregoing applications are hereby incorporated by reference.

FIELD OF THE INVENTION

Aspects of the present invention relate generally to archival and retrieval of sample material, and more particularly to a system and method of storing a solid medium in a sealed storage element and removing same therefrom.

DESCRIPTION OF THE RELATED ART

In many applications such as pharmaceutical and medical research, law enforcement, and military identification, for example, it is often desirable to have access to numerous biological samples. Conventional biorepositories or other sample storage facilities typically utilize liquid or other low temperature cryogenic systems for sample storage; these cryogenic systems are expensive both to create and to maintain. Additionally, current technology generally presents system operators with complicated and labor intensive maintenance and administrative responsibilities.

Specifically, the intricacies of cryogenic systems may typically oblige technicians, researchers, and system operators to engage in coordinated labor for weeks to retrieve and to prepare thousands of deoxyribonucleic acid (DNA) samples from whole blood. Accordingly, conventional approaches for archiving DNA in cryogenic states are fundamentally inadequate to the extent that they do not accommodate high volume processing and sample throughput. Current research trends recognize benefits associated with systems and methods of archiving and retrieving biological and non-biological samples which may be capable of processing thousands of samples per day; current cryogenic technology, however, is inadequate to attain throughput at this level. In fact, cryogenic storage facilities cannot accommodate processing throughput of one hundred or more samples per day from tens of thousands of archived samples.

Although some low throughput liquid-state DNA and blood archival techniques have been useful in the past, present methodologies are not capable of supporting the increasing storage and retrieval rates required as advancing genomics technology becomes more prevalent as a research and diagnostic tool. Since the traditional cryogenic-based archival format is difficult and expensive to automate, systems based upon existing technology are generally not amenable to the high throughput demands of the market.

Recently, biological research laboratory systems have been proposed which incorporate archival and retrieval of blood samples in dry or desiccated form. Typical systems employing conventional technology are generally based upon modifications or variations of known techniques for storing DNA or other organic samples on a suitable substrate such as filter paper. Improved systems and methods incorporating automated archival and retrieval of biological and non-biological sample material have been disclosed in the related co-pending applications noted above.

In particular, full automation of the storage and retrieval processes in sample archival systems may employ robotics and other machinery operating repeatedly to identify, to retrieve, and to replace individual storage elements within a large volume storage room or vault.

In a storage and retrieval system, it is usually important for economic reasons to maximize the storage density, i.e. the quantity of items stored per unit volume, footprint area, or cost. Conventional commercial storage and retrieval systems usually consist of an array of bins, shelves, or trays mounted in a regular array with some mechanism for retrieving an individual storage element and placing it in a position where a robot or an operator can select samples. Common automated embodiments include:

- carousels, in which rows or columns of storage elements are connected in a loop and rotated past a window;
- vertical lifts, in which the storage element is embodied in a removable unit located in a rack, and wherein an elevator mechanism removes a selected unit from the rack and translates it to a fixed window for use; and
- pigeonholes, generally comprising a planar array of slots, each of which may store one item or storage element.

Pigeonhole systems are most commonly used in situations where each of the plurality of items to be stored is similar in size and shape. In this case, a Cartesian manipulator traverses the array to move items between the pigeonholes and a fixed access point. Typically, there are two planes of slots, analogous to a pair of facing bookshelves.

Conventional commercial versions of such storage systems are supplied at a fixed minimum pitch, or spacing between storage elements. When storing items which have a thickness less than the minimum pitch, storage density is reduced due to wasted space between storage elements. Significantly improved archival and retrieval systems and methods are disclosed in co-pending application Ser. No. 10/252,352, filed Sep. 20, 2002, entitled "SYSTEM AND METHOD OF STORING AND RETRIEVING STORAGE ELEMENTS;" these systems and methods allow greater use of available volume for storing laboratory storage elements and other regularly shaped objects.

What is needed is a sealed storage element system and method configured and operative for use in conjunction with numerous laboratory and archive facilities having various design configurations and differing operational characteristics.

SUMMARY

Embodiments of the present invention overcome the foregoing and various other shortcomings of conventional technology, facilitating storage and removal of a sample carrier with respect to a sealed storage element.

As set forth in detail below, some embodiments of a sealed storage element may generally comprise a container having a reception opening configured and operative to receive a sample carrier and an ejection opening configured and operative to allow ejection of the sample carrier. Such a storage element may further comprise a first film applied to a first surface of the storage element and sealing the ejection opening. Depending upon system requirements, the first film may be radio frequency transparent or optically transparent.

Additionally, a storage element may further comprise a second film applied to a second surface of the storage element and sealing the reception opening. As with the first film, the second film may be radio frequency transparent or optically transparent.

In some embodiments of a storage element, at least one of the first film and the second film may be polymeric; additionally or alternatively, at least one of the first film and the second film may be metallic. The storage element may be generally constituted such that the container is a well of a multi-well plate, and may further comprise identifying indicia; in some embodiments, the indicia may comprise a bar code.

In accordance with one exemplary embodiment, a storage element as illustrated and described herein may generally comprise a plurality of containers; each of the plurality of containers having a respective reception opening configured and operative to receive a sample carrier and a respective ejection opening configured and operative to allow ejection of the sample carrier. The plurality of containers may be arranged in a predetermined spatial relationship. The storage element may generally be constituted such that each of the plurality of containers is a well of a multi-well plate, and may further comprise identifying indicia. The identifying indicia may comprise or be embodied in a bar code, for example.

As set forth below, such an embodiment of a storage element may further comprise a first film applied to a first surface of the storage element and sealing the respective ejection opening of selected ones of the plurality of containers. Additionally, the storage element may further comprise a second film applied to a second surface of the storage element and sealing the respective reception opening of selected ones of the plurality of containers.

At least, one of the first film and the second film may be radio frequency transparent; additionally or alternatively, at least one of the first film and the second film may be optically transparent. In accordance with some exemplary embodiments, at least one of the first film and the second film may be polymeric or metallic.

In accordance with one embodiment set forth in detail below, a method of archiving a sample may comprise: providing a storage element comprising a container having a reception opening configured and operative to receive a sample carrier and an ejection opening configured and operative to allow ejection of the sample carrier; sealing the ejection opening; inserting a sample carrier into the container through the reception opening; and archiving sample material maintained on the sample carrier in the container.

Such a method of archiving may further comprise sealing the reception opening subsequent to the inserting. In some embodiments, an archiving method may further comprise loading the sample carrier with specimen material; the loading may comprise providing specimen material to the container through the reception opening. Similarly, the method may further comprise providing preservatives to the container through the reception opening.

As set forth in detail herein, sealing the ejection opening may comprise applying a first film to a first surface of the storage element; in some embodiments, such applying comprises bonding the first film around the perimeter of the ejection opening. Similarly, sealing the reception opening may generally comprise applying a second film to a second surface of the storage element; in this instance, such applying may comprise bonding the second film around the perimeter of the reception opening.

Additionally, a method of archiving in accordance with the present disclosure may further comprise selectively orienting the sample carrier subsequent to the inserting. The orienting may comprise exerting a magnetic force on the sample carrier; in turn, the exerting may comprise applying a magnetic field to the storage element.

In accordance with additional embodiments set forth in detail below, a method of inserting a sample carrier into a storage element generally comprises: providing a storage element comprising a container having a reception opening configured and operative to receive a sample carrier and an ejection opening configured and operative to allow ejection of the sample carrier; providing a substrate comprising a sample storage medium; selectively cutting a sample carrier from the substrate; and inserting the sample carrier into the container through the reception opening.

In some embodiments, the method of further comprises sealing the ejection opening prior to the inserting. Additionally or alternatively, the method may further comprise sealing the reception opening subsequent to the inserting.

As set forth in the following detailed description, the selectively cutting may comprise utilizing a cutting template influencing a dimension of the sample carrier; further, the inserting may comprise utilizing a retention template dimensioned in accordance with the reception opening and the cutting template. The inserting may further comprise utilizing a plunger to advance the sample carrier through the retention template and through the reception opening.

Additionally, the method of inserting a sample carrier into a storage element may further comprise loading the sample carrier with specimen material subsequent to the inserting. In some embodiments, the loading comprises providing specimen material to the container through the reception opening.

As set forth below, methods are disclosed wherein the substrate comprises a cellulose sample support medium such as filter paper. Additional methods are disclosed wherein the substrate comprises a polymeric sample support medium such as polyurethane.

Sealing the ejection opening may comprise applying a first film to a first surface of the storage element, and sealing the reception opening may comprise applying a second film to a second surface of the storage element.

As with archiving a sample carrier, a method of inserting a sample carrier into a storage element may further comprise selectively orienting the sample carrier subsequent to the inserting; embodiments are disclosed wherein the selectively orienting comprises exerting a magnetic force on the sample carrier. The exerting, in turn, may comprise applying a magnetic field to the storage element.

As illustrated and described in detail below, a method of ejecting a sample carrier from a sealed storage element may comprise: providing a storage element comprising a container having a reception opening configured and operative to receive a sample carrier and an ejection opening configured and operative to allow ejection of said sample carrier; aligning an ejector with the container; inserting the ejector through the reception opening; and ejecting the sample carrier from the container through the ejection opening.

Embodiments of the foregoing method are disclosed wherein the storage element comprises a plurality of containers and wherein the method further comprises identifying a location of a target sample carrier in the storage element. The identifying and the aligning may further comprise utilizing a signal received from a transceiver co-located with the target sample carrier. In accordance with some exemplary methods, the transceiver is activated by radio frequency energy or by optical energy.

As with the embodiments noted above, a method of ejecting a sample carrier from a sealed storage element may further comprise selectively orienting the target sample carrier;

this orienting may occur prior to the utilizing. Selectively orienting may comprise exerting a magnetic force on the target sample carrier.

In some disclosed methods, the inserting comprises piercing a film sealing the reception opening, and the ejecting comprises piercing a film sealing the ejection opening. Additionally, methods are disclosed comprising providing a daughter plate to receive the sample carrier responsive to the ejecting.

In accordance with some embodiments, an archive system as illustrated and described herein generally comprises: a receptacle having a support surface; a plurality of storage elements arranged in a two dimensional configuration on the support surface, each of the plurality of storage elements comprising a container having a reception opening configured and operative to receive a sample carrier and an ejection opening configured and operative to allow ejection of the sample carrier; and an ejector apparatus. The ejector apparatus is operative to: align an ejector with a target container in a selected one of the plurality of storage elements; insert the ejector through the reception opening in the target container; and eject the sample carrier from the target container through the ejection opening.

The archive system may further comprise a handling apparatus selectively operative to engage targeted ones of the plurality of storage elements. In some archive systems, each of the plurality of storage elements is oriented on end; embodiments of such an archive system are disclosed wherein each of the plurality of storage elements is sealed at the reception opening and at the ejection opening.

The foregoing and other aspects of various embodiments of the present invention will be apparent through examination of the following detailed description thereof in conjunction with the accompanying drawings.

BRIEF DESCRIPTION OF THE DRAWINGS

FIGS. 6A-6C represent a series of simplified transverse cross-sectional diagrams of one embodiment of a system configured and operative to eject a sample carrier from a storage element.

DETAILED DESCRIPTION

A system and method operative in accordance with the present disclosure facilitate storage and retrieval of individual or discrete samples of biological, non-biological, and chemical material stored on dry media which may be either solid or porous. In accordance with some embodiments, sample material may be disposed upon or within a porous or solid (i.e., non-porous) sample storage medium and subsequently archived in, and retrieved from, storage elements such as multi-well plates, for example, using robotic devices or other automated apparatus. The storage medium may be selectively transferred, contamination free, from a sealed storage element to a selected well in a daughter plate, for example, or to another suitable container or receptacle when recovery of the sample material is desired.

In that regard, the disclosed apparatus and system enable ejection of sample material from a sealed storage element into a specific well of a multi-well daughter plate, or into a specific cuvette, test tube, or similar container. In some embodiments, a sample carrier comprising a storage medium may be punched or ejected through a first seal of the storage element with an apparatus or implement such as a disposable piercing tip, for instance, inserted through a second seal of the storage element.

Accordingly, a sample storage element may comprise or be embodied in a bottomless multi-well plate wherein each well, or container, of the plate may be configured and operative to contain a discrete sample. A first sealing film may seal a first surface, such as the bottom, for example, of the storage element. A discrete sample (which may be disposed on, or carried by, a sample storage medium at a discrete sample node as described below, for example) may be introduced into a respective container of the storage element. A second sealing film may seal a second surface, such as the top of the storage element, for example, to protect the sample from contamination or degradation.

A semi-rigid rod, wire, or similar elongate member may selectively pierce the films, ejecting the sample carrier disposed in a particular target container or well in the storage element. The material selected for the ejector may generally be rigid enough to pierce the sealing films, but soft enough to allow a sharp bias cut. In some embodiments, the ejector may be constructed of low cost and disposable materials such as plastics or other polymers.

Figure 1A:
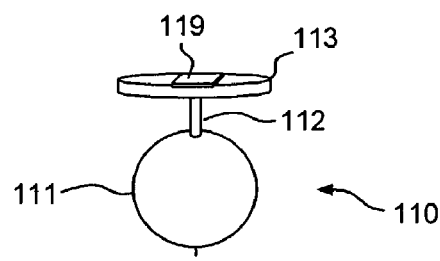
FIG. 1A is a simplified diagram illustrating one embodiment of a sample carrier configured and operative for use in conjunction with a storage element.

Turning now to the drawings, FIG. 1A is a simplified diagram illustrating one embodiment of a sample carrier. As illustrated in FIG. 1A, a sample carrier 110 may generally comprise a sample node 111 operative to carry a discrete sample and a sample identifier 119 operative to provide information associated with the discrete sample carried at node 111.

As indicated in FIG. 1A, carrier 110 may include one or more physical structures, such as stem 112, configured and operative to support an identification and handling structure 113 to which identifier 119 may be attached. It is noted that the depiction of carrier 110 is representative only, and that, in particular, the characterization of stem 112 and identification structure 113 is not intended to be interpreted in any limiting sense. Specifically, as set forth in more detail below with reference to FIGS. 2A-2F, the structural arrangement of the components of sample carrier 110 is susceptible of various modifications and alterations depending upon, among other things, the material from which the components are fabricated, the functionality of any automated handling mechanisms with which carrier 110 is intended to be used, and the structural characteristics of a storage element with which carrier 110 is intended to be engaged as set forth in more detail below.

In that regard, the relative proportions, size, length, diameter, and other physical characteristics of stem 112 and identification structure 113 may be selected in accordance with the intended use of carrier 110. In some embodiments, for example, carrier 110 may be grasped and transported or otherwise manipulated by robotic gripping mechanisms, vacuum or magnetic chucks, or other automatic apparatus; accordingly, identification structure 113 and stem 112 may constructed of suitable material and be so dimensioned as to provide sufficient rigidity and structural integrity to withstand any external forces exerted by automatic handling or gripping devices on identification structure 113. Similarly, as set forth herein, carrier 110 may be configured and operative to engage a storage element (such as represented by reference numeral 120 in FIG. 1B, for example) during use; accordingly, the length of stem 112 and the diameter and thickness of identification structure 113 may be suitably dimensioned to facilitate interoperation of carrier 110 with such a storage element.

Structural elements of carrier 110 may be constructed of any material with sufficient rigidity to enable the manipulation and transport of carrier 110 by robotics or other automated mechanisms as described above. It will be appreciated that the structural elements of carrier 110, including sample node 111, may be formed or molded as an integrated unit, for example; in some embodiments, carrier 110 may be fabricated using injection molding techniques generally known in the art, for instance. Alternatively, some or all of the components may be fabricated individually and subsequently attached, adhered, fused, joined, or otherwise integrated to form a unified structure for carrier 110. Sample node 111, stem 112, and identification structure 113 may be fabricated of polystyrene or various plastics, for example, such that the overall structure of carrier 110 is afforded suitable stiffness without rendering carrier 110 unnecessarily heavy or cumbersome. It will be appreciated that various fabrication techniques generally known in the art may be used to construct carrier 110 and the various components illustrated in FIG. 1A. The present disclosure is not intended to be limited to any particular materials or construction methods employed with respect to fabrication of carrier 110.

As noted generally above, the exemplary embodiment of carrier 110 generally comprises sample node 111 operative to carry a discrete sample and identifier 119 operative to provide information associated with the discrete sample carried at node 111. In the illustrated arrangement, identifier 119 is co-located with the sample it identifies.

The term "co-located" in this context generally refers to the location of both the sample and identification or other information associated with the sample. For instance, identifier 119 may be attached, adhered, fused, coupled, or otherwise connected to node 111 as described above, for example, via suitable components such as stem 112 and identification structure 113; alternatively, as described in detail below with reference to FIGS. 2A-2C, identifier 119 may be integral with or incorporated into the structure of node 111 itself such that supporting or attaching structures may be omitted.

Figure 2A:
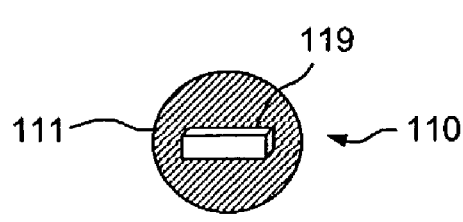
FIGS. 2A-2F are simplified illustrations representing embodiments of a sample carrier.
Figure 2B:
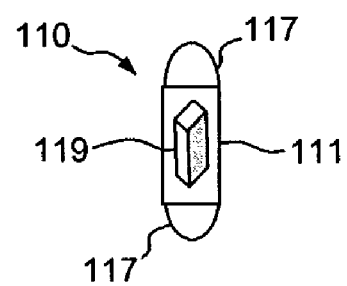
Figure 2C:
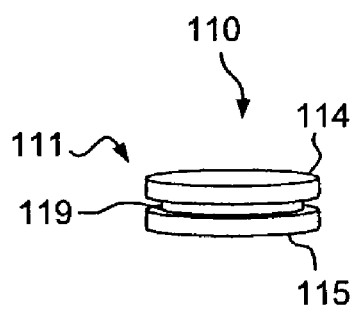

In that regard, identifier 119 and node 111 may be "permanently" co-located such as through physical attachment (FIG. 1A) or through integration of identifier 119 with node 111 (FIGS. 2A-2C). Accordingly, unique identification information and other data may be co-located with the sample carried at node 111 throughout the useful life of sample carrier 110 (i.e., until sample material is removed or extracted from node 111 for experimentation or other uses).

Permanently co-locating node 111 and identifier 119 substantially as set forth herein may ensure that information associated with a particular discrete sample is always available at the location of that sample. Accordingly, handling errors (arising for example, due to misplacement of node 111) may be minimized or eliminated, since the sample at node 111 may be identified by reference to identifier 119, and since identifier 119 is integrated with or connected to node 111.

It will be appreciated that sample node 111 may be substantially spherical as represented in FIG. 1A; alternatively, node 111 may be formed in any of numerous shapes and sizes; by way of example, several possibilities are illustrated in FIGS. 2A-2F. Those of skill in the art will appreciate that several polygons, polyhedrons, pyramidal or triangular shapes, disks, or oblong embodiments are contemplated and may be selected based upon various factors such as the desired node size and density, the saturation limit of the material used for sample node 111, the accuracy and precision of the device used to manipulate sample carrier 110, and the like. The present disclosure is not intended to be limited by the shape, size, or dimensional characteristics of sample node 111.

Sample node 111 may bind sample material directly or indirectly. In that regard, an exemplary node 111 may generally comprise, or be constructed entirely of, a sample support medium. In some embodiments, for example, node 111 may simply be coated with a selected sample support medium such that node 111 binds a sample indirectly; alternatively, the entire structure of node 111 may be fabricated of a sample support medium (i.e., sample support medium may constitute the structure of node 111) to bind the sample directly. In accordance with one aspect of the present invention, sample support media for use at sample node 111 may be embodied in paper or cellulose, polymers such as polystyrene or chitosan, plastics, ceramics, or other suitable support material constructed and operative to serve as a long-term storage mechanism for biological or other sample material. Specimen material in solid, liquid, or gaseous form may be brought into contact with the sample support medium and stored as a sample at discrete sample node 111.

In some embodiments, for example, such a sample support medium may maintain samples of biopolymers, including polynucleotides such as ribonucleic acid (RNA) and deoxyribonucleic acid (DNA) as well as proteins, or non-biological samples, including fluorocarbons or chlorofluorocarbons (CFCs), environmental pollutants, and synthetic chemical compounds. As noted above, filter paper substrate embodiments are currently known in the art; for example, U.S. Pat. No. 6,294,203 discloses a dry solid medium for storage of sample material which may be suitable for incorporation into sample carrier 110. The disclosure of this United States Patent is hereby incorporated by reference in its entirety.

The present disclosure is not intended to be limited with respect to specific sample support media employed at node 111. Accordingly, a support medium suitable for implementation at sample node 111 may generally comprise any appropriate material known in the art or developed and operative in accordance with known principles, and may be selected in accordance with binding properties as a function of the type of sample to be carried and maintained.

In that regard, an appropriate sample support medium may be solid or porous, for example, depending, in part, upon the type of specimen to be stored as a sample at node 111. Additionally or alternatively, the sample support medium may be treated with one or more chemical compounds or derivatized, for instance, to manipulate various binding properties prior to contact with a specimen. Positive or negative electrical charges, chemical compositions, binding characteristics, antibodies, lectins, porosity, and other operational factors for sample node 111 may be selected in accordance with the type of sample support medium implemented and the type or nature of any processes performed thereon.

Figure 1B:
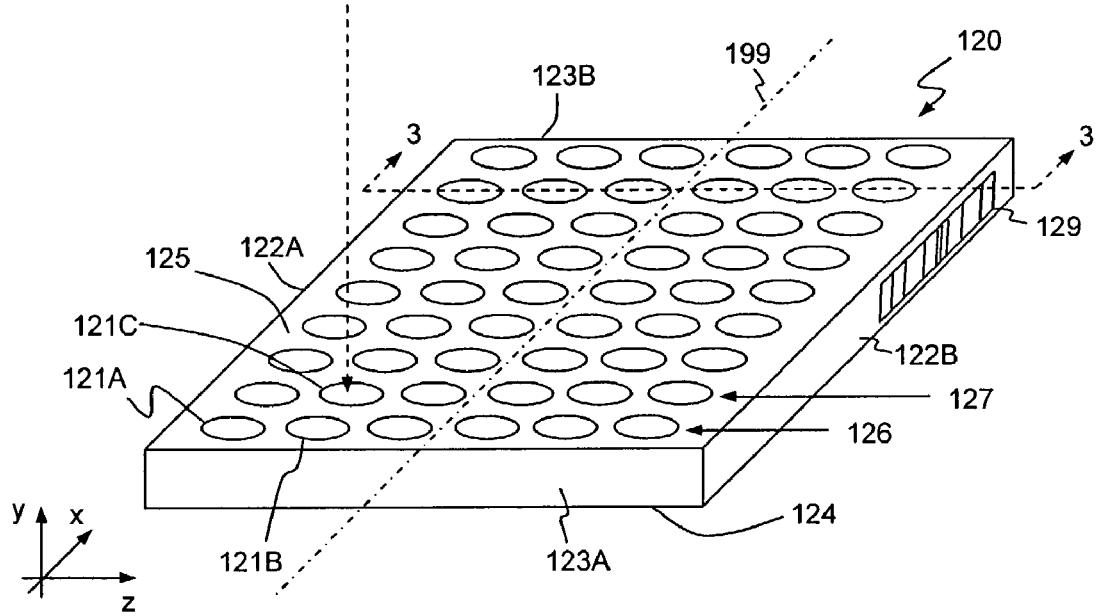
FIG. 1B is a simplified diagram illustrating one embodiment of a storage element configured and operative for use in conjunction with a sample carrier.

Biological and non-biological samples may be stored in a controlled environment. In that regard, humidity, temperature, and other environmental factors may be controlled in a fireproof vault or other structure employed as an archive. In some embodiments, environmental conditions may be selectively altered depending, for instance, upon the nature of the samples, the composition of the sample support medium employed at sample node 111, or both, to preserve longevity of the samples for decades. In a biopolymer (such as a polynucleotide) archival embodiment, for example, the sample support medium may include a chemically treated surface or structure, serving to lyse particular specimen cells and to immobilize the polynucleotide structure to the sample support medium or substrate at discrete sample node 111. Additionally or alternatively, preservatives may be applied, embedded, impregnated, or otherwise incorporated onto or into the sample support medium; such preservatives may ensure the stability and fidelity of the polynucleotide structure for tens of years. Sample node 111, which may be characterized by a discrete pellet or sphere as represented in FIG. 1A, may be selectively deposited in a particular well disposed in a multi-well plate as represented in FIG. 1B; samples deposited in particular wells may, in turn, be selected for subsequent processing (e.g., such as with polymerase chain reaction (PCR) assays, and the like).

Cross contamination may be virtually eliminated by storing a sample on node 111. In some instances, mechanical contact involving a mechanical sample removal device may be minimized or entirely eliminated during retrieval, extraction, purification, packaging, and shipping. Moreover, since carrier 110 or handling and identification structure 113 may be amenable to manipulation by standard robotics, an entire archive facility may be easily automated to achieve high throughput rates (for example, greater than one hundred samples per day).

Polynucleotides such as DNA or RNA archived and retrieved using sample carrier 110 as set forth above may be well suited for large-scale genetic analysis, and may yield samples which are superior (relative to conventional liquid phase or cryogenic technologies) for pharmacogenetics or other types of genetic discovery analyses. Specifically, implementation of sample node 111 may automatically standardize the quantity and quality of polynucleotide storage due to the inherent loading properties of the sample support medium and any embedded chemicals serving to diminish PCR inhibitors; accordingly, the requirements and complexities of quantification procedures following purification in conventional polynucleotide extraction may be simplified, reduced, or eliminated entirely. Additionally, dry or desiccated archive samples are not continuously degraded during repeated freezing and thawing cycles as is common in cryogenic systems.

In operation, identifier 119 may generally maintain or provide information associated with the discrete sample carried at node 111. In some embodiments, identifier 119 may enable access to such information, maintaining or providing a unique code, serial number, or other identifying indicia associated with the sample; in such embodiments, a database or other record store may be interrogated or queried for information associated with the sample using the code or signal displayed or provided by identifier 119.

In this context, therefore, and to simplify further discussion, it will be appreciated that the functionality of identifier 119 referred to as "providing" information associated with a sample generally encompasses, without limitation: maintaining or storing such information, in whole or in part, at identifier 119; communicating, transmitting, or otherwise conveying such information, in whole or in part, from identifier 119; and reflecting, signaling, transmitting, or otherwise communicating a unique code, signal, data stream, or other indicator operative to identify the sample and to enable access to such information.

In the FIG. 1A embodiment, for instance, identifier 119 generally comprises identifying indicia by which a sample carried at node 111 may be uniquely identified. In that regard, identifier 119 may comprise a one- or two-dimensional bar code having light and dark areas of varying width and separation as is generally known in the art. Additionally or alternatively, identifier 119 may comprise a serial number, lot number, alpha-numeric code, or other symbolic representation suitable to identify or to distinguish sample material carried at node 111. Such bar codes or other identifying indicia may be scanned by any of various machine vision or other optical sensors or reading devices generally known in the art. In these embodiments, identifier 119 may maintain or provide a unique sample identification encoded in the bar code or identifying indicia; accordingly, information associated with the sample at node 111 may be obtained or accessed using the unique identifying data or symbolic representation encoded in the indicia.

In some embodiments, for example, optical reading equipment may generally comprise machine vision technology, video cameras, or other optical sensors which are capable of identifying or locating the elements represented in the bar code or other indicia of identifier 119 using instruments or receptors which are sensitive to various portions of the electromagnetic spectrum. In this embodiment, optical information (from the visible portion of the spectrum) or other electromagnetic information (such as microwave, infrared, or radio frequencies, for example) may be used to ascertain the identity, nature, and general constitution of the co-located sample carried at node 111.

In particular, identifier 119 may be embodied in a miniature light-activated transponder or transceiver, for example. As is generally known in the art, visible, fluorescent, or coherent light or other suitable optical energy of a selected wavelength and frequency delivered by an appropriate source such as a laser, for example, may provide energy to photovoltaic cell incorporated in identifier 119. In this embodiment, optical energy captured or received at such a cell may power a microcontroller or microchip, additional circuitry and associated electronic memory, and a transmitter. Alternatively, radio frequency (RF) energy may be used to activate a transceiver at identifier 119.

As is generally known in the art, a microchip in identifier 119 may access memory, retrieve information associated with the co-located sample carried at node 111, influence operation of a transmitter, and enable transmission of a signal representative of the information associated with the sample. Alternatively, the transmitter may transmit a distinct or unique identifier code or signal associated with the co-located sample at node 111; data records and other information regarding the sample carried at node 111 may be accessed by another device in a remote location, for example, in accordance with the identification signal transmitted or broadcast by the transmitter.

Sample identification and other information maintained and provided by identifier 119 may generally include, but is not limited to: a distinct identifier code or other indicia enabling accurate identification and tracking of the sample; the nature or type of sample (e.g., blood, DNA, RNA, protein, environmental particles, or pollutants); the source or origin of the sample (e.g., age, gender, and medical history of a person, or the location and circumstances under which an environmental sample was collected); the time and date the sample was collected or archived; and the like. Data records or other structures representative of this information may be encoded in identifier 119 itself, for example, or may be maintained in a database or other data storage structure or facility.

In some implementations, sample carrier 110 may be designed or configured to engage a sample container such as a well in a standard or modified multi-well plate. When carrier 110 is engaged with such a container or storage element, node 111 may be brought into contact with specimen material in the well; additionally or alternatively, carrier 110 may engage a clean or unused well (i.e., one containing no specimen material or traces of contaminants) such that the sample material at node 111 may be stored and cross-contamination between samples carried at individual sample nodes may be prevented.

FIG. 1B is a simplified diagram illustrating one embodiment of a storage element. In the illustrated embodiment, storage element 120 generally comprises a plurality of sample containers or wells 121 arranged in a predetermined orientation relative to a longitudinal axis 199. Each well 121 may be configured and operative to receive a sample carrier 110, and more particularly, a sample node 111 substantially as described above.

It will be appreciated by those of skill in the art that the FIG. 1B embodiment of storage element 120 is illustrated by way of example only, and not by way of limitation. Various shapes of storage element 120 and configurations of wells 121 are within the scope and contemplation of the present disclosure. While a rectangular configuration is illustrated and described herein, for example, storage element 120 may alternatively be generally circular, square, or polygonal in plan, depending for example, upon the requirements or configuration of the laboratory or archive facility in which storage element 120 is utilized.

In an exemplary rectangular embodiment, storage element 120 generally comprises longitudinal sides 122A, 122B and transverse sides 123A, 123B. Those of skill in the art will appreciate that scientific sample storage and experimentation systems may employ robotic mechanisms for grasping, translating, or otherwise manipulating multi-well plates in a laboratory or sample archive facility. Accordingly, sides 122A-B, 123A-B may be shaped and dimensioned such that suitable gripping or handling mechanisms (whether manual or automated) may engage storage element 120 for appropriate or desired manipulation.

In that regard, storage element 120 may generally be fabricated of any suitable material providing sufficient rigidity and strength to withstand forces exerted by such automated or robotic systems. It may also be desirable to construct storage element 120 of material which will not contaminate any sample or specimen material contained in wells 121. Various plastics, ceramics, polystyrenes, and polymeric or other materials generally known in the art for constructing multi-well plates may be suitable for wells 121 and other components of storage element 120.

Storage element 120 may be fabricated as a single unit, for example, or may generally comprise two or more pieces fabricated individually and subsequently joined, adhered, or otherwise connected. In that regard, some embodiments of storage element 120 may generally comprise a frame structure (not shown) configured and operative to receive discrete rows (such as 126 and 127, for example) of wells. In accordance with this aspect, rows 126 and 127 may be individually fabricated and employed independently as is generally known in the art.

Additionally, storage element 120 may be constructed and operative to support a label, tag, decal, or other identifying indicia 129 which may be unique to storage element 120. As is generally known in the art, identifying indicia 129 may incorporate a bar code (e.g., either one- or two-dimensional), a serial number, or other alpha-numeric or symbolic representation, for example, and may distinguish each particular storage element 120 from others maintained in an archive or laboratory facility. In such an embodiment, indicia 129 may be placed or oriented on a selected side 122A-B, 123A-B such that indicia 129 are neither obscured nor marred by robotics or other mechanisms designed to handle storage element 120.

With reference now to both FIGS. 1A and 1B, it will be readily apparent that carrier 110 and storage element 120 may be constructed and dimensioned such that sample node 111 is supported in a predetermined spatial relationship relative to specimen material contained in a respective container (such as well 121C) for "loading" node 111 with sample. By way of example, sample node 111 may be placed in a position to contact specimen material in well 121C. Additionally, carrier 110 may be deposited in a respective container (such as well 121C) for storage; as set forth in more detail below with reference to FIGS. 3A and 3B, carrier 110 may be placed or deposited in a clean or sterilized well 121C and sealed therein for archiving. In that regard, storage element 120 may be configured and operative to isolate a plurality of sample carriers 110 from each other and to seal off each sample carrier 110 from external contaminants.

In accordance with some embodiments, each well 121 or specimen container in storage element 120 may generally comprise a reception opening configured and operative to receive a sample carrier 110 and an ejection opening configured and operative selectively to allow ejection of the sample carrier 110; this ejection may be executed in cooperation with an ejector (described below). In such an arrangement, storage element 120 may be sealed, both on a first surface 124 as well as on a second surface 125, as set forth in more detail below.

Those of skill in the art will appreciate that storage element 120 may include or be configured to accommodate a lid or cover (not shown) such as generally used in conjunction with multi-well plates. In some embodiments, indicia 129 may be placed or oriented such that a cover, when operatively engaged with storage element 120, does not obscure indicia 129; alternatively, a cover for use with storage element 120 may be modified or specifically constructed so as not to obscure indicia 129. In embodiments of storage element 120 comprising a sealing film (sealing, for example, second surface 125) or other structural element preventing contamination of wells 121, a lid or cover may not be required to ensure sample integrity.

FIGS. 2A-2F are simplified illustrations representing embodiments of a sample carrier. The embodiments of sample carrier 110 depicted in FIGS. 2A-2F generally correspond with those described above with reference to FIGS. 1A and 1B, and may incorporate some or all of the structural elements and functional characteristics set forth in detail above.

In FIG. 2A, for instance, node 111 may generally correspond to that described in detail above. Identifier 119 may be incorporated in node 111; in the exemplary FIG. 2A embodiment, identifier 119 may comprise a miniature radio frequency (RF) activated transponder or transceiver, for example. As is generally known in the art, RF energy of a selected wavelength and frequency delivered by an appropriate source such as an antenna, for example, may be received by a suitable antenna and provide energy to an RF cell incorporated into or operatively coupled to identifier 119. In this embodiment, RF energy captured by such an antenna and received at the cell may power a microcontroller or microchip, additional circuitry and associated electronic memory, and a transmitter substantially as described above with reference to FIG. 1A.

As described above, a microchip may access memory, retrieve information associated with the co-located sample carried at node 111, and facilitate transmission of a signal representative of the information associated with the sample. In some embodiments, the transmitter may transmit a distinct or unique identifier code or signal associated with the co-located sample at node 111; accordingly, data records and other information regarding the sample carried at node 111 may be accessed by another device in a remote location, for example, responsive to the identification signal transmitted or broadcast by the transmitter.

With reference now to FIG. 2B, identifier 119 may generally correspond to those described above; specifically, identifier 119 may incorporate or comprise an RF activated transceiver. In the exemplary FIG. 2B embodiment, identifier 119 may be incorporated into or integrated with the structure of node 111.

As with the implementations described above, applied electromagnetic energy may power the transceiver which comprises an appropriate receiving antenna and a tuned capacitor (not shown). The capacitor may drive electronics, including a transmitter, which in turn may transmit a distinct or unique RF signal or code identifying the co-located sample carried at node 111.

In the foregoing embodiment, the transceiver may be embedded within the sample support medium of node 111; alternatively, node 111 may be fabricated or constructed as a sheath or sleeve configured and operative to surround at least a portion of identifier 119. In some embodiments, for example, it may be desirable to limit the extent to which node 111 envelopes identifier 119; where node 111 is confined or limited to a portion of identifier 119 or a housing (such as indicated by reference numeral 117) of the transceiver, sample carrier 110 may be manipulated, mechanically or otherwise, at the ends of housing 117 without the risk that the handling device or grasping apparatus will make contact with, and potentially contaminate, the sample carried at node 111.

Sample carrier 110 such as depicted in FIG. 2B may be sized and dimensioned to engage a well 121 of a storage element 120. It will be appreciated that carrier 110 may additionally comprise a gasket or other structure (not shown) operative to engage such a well 121, simultaneously supporting carrier 110 in a position allowing node 111 to contact liquid specimen and preventing contamination by precluding introduction of particulate matter to well 121 when carrier 110 is engaged with storage element 120. Alternatively, the FIG. 2B embodiment of sample carrier 110 may be appropriately sized and dimensioned to fit entirely within a suitable container in a storage element 120.

FIG. 2C is a simplified diagram illustrating another embodiment of a sample carrier configured and operative for use in conjunction with the embodiments of an RF activated transceiver described above. In the exemplary FIG. 2C arrangement, node 111 generally comprises a first layer 114 and a second layer 115 of sample support medium. Identifier 119 generally comprising a transceiver such as described above may be interposed between layers 114 and 115. In some embodiments, layers 114 and 115 may be fabricated of filter paper or another suitable substrate such as the support medium disclosed in U.S. Pat. No. 6,294,203, incorporated by reference above.

As noted above, layers 114, 115 may be embodied in filter paper or other porous material; it will be appreciated, however, that layers 114, 115 may alternatively be constructed of or comprise solid or non-porous material suitable to be used as a sample support medium. In that regard, any of the various sample support media set forth above may be suitable for layers 114, 115, and may be selected in accordance with fabrication techniques or other factors such as the operational characteristics of the automated handling mechanisms with which sample carrier 110 is intended to be used.

In some implementations, for example, it may be desirable to provide layers 114, 115 with sufficient rigidity to withstand manipulation by robotics or other handling mechanisms; such mechanical gripping apparatus, however, may potentially introduce contamination to the sample carried at node 111. Alternatively, identifier 119 housing or comprising a transceiver may be provided with sufficient thickness to accommodate such a gripping or handling device, such that layers 114, 115 are not contacted by any portion of the apparatus handling carrier 110.

As set forth in detail above with reference to FIG. 1A, an identifier 119 comprising a transceiver may be incorporated into, or attached, adhered, or otherwise affixed to, an identification structure 113. Additionally or alternatively, an identifier 119 may be integrated with the structure of node 111 as indicated in FIGS. 2A-2C. Implementation of a transceiver which is responsive to RF signals, as opposed to optical energy, for example, further facilitates the embodiments illustrated in FIGS. 2A-2C. Since the microchip and other components of an RF activated transceiver are not dependent upon optical energy for operating power, for example, identifier 119 comprising such a transceiver may be entirely integrated or contained within the structure of node 111. Accordingly, the exemplary embodiments of FIGS. 2A-2C may not include any structural components (such as stems or identification structures, for example) attached or otherwise external to node 111.

Further, it will be appreciated that one or more additional identifiers 119 may be implemented in conjunction with carrier 110 depending, for example, upon the sophistication or functional characteristics of the transceiver, the operational requirements of the system in which carrier 110 is employed, or a combination of both. Specifically, any of the embodiments illustrated and described with reference to FIGS. 2A-2F, for example, may incorporate structural elements and sample identification strategies illustrated and described above with reference to FIG. 1A. Those of skill in the art will appreciate that any number of features and aspects of the disclosed embodiments may readily be combined or interchanged depending upon, among other things, the desired functionality of carrier 110, structural features of the storage element 120 or functional aspects of the automated equipment with which carrier 110 is implemented, the nature and chemical properties of the sample carried at node 111, and so forth.

It is also noted that various types of transponders or transceivers such as those described above are currently known and employed in a wide variety of applications. For example, numerous transponders such as those described as incorporated into identifier 119 are presently implanted in animals and are employed for identifying lost pets. Additionally, various micro-transceiver systems have been developed by researchers and proposed for use in active drug delivery techniques. Micro-transceivers or transponders such as described above may generally be operative to transmit omni-directional RF signals, for example, enabling a receiver to locate and to identify the sample carried at node 111 using associated signature signal frequencies, transmission patterns, or other information. Accordingly, a unique signal transmitted by a transceiver incorporated into identifier 119 may be used to direct the positioning of robotic instrumentation or sample handling apparatus.

Figure 2D:
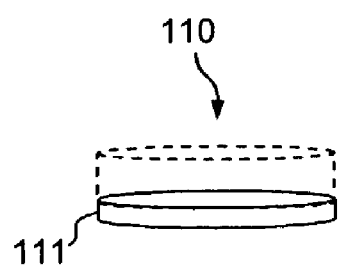

FIG. 2D is a simplified diagram illustrating another embodiment of a sample carrier. Sample carrier 110 generally comprises a sample node 11 operative to carry a discrete sample; in that regard, node 111 may comprise or be embodied in a suitable sample support medium. As set forth above, node 111 may be coated with a selected sample support medium such that node 111 binds a sample indirectly; alternatively, the entire structure of node 111 may be fabricated of a sample support medium (i.e., sample support medium may constitute the structure of node 111) to bind the sample directly.

As described above, sample support media for use at sample node 111 may generally be embodied in chitosan, plastic, ceramic, polystyrene or other polymers, or any other suitable support material constructed and operative to serve as a long-term storage mechanism for biological or other sample material. In the FIG. 2D embodiment, node 111 is embodied in such a sample support medium, and may generally be constructed of paper or cellulose, or a polymer such as polyurethane foam having high porosity and pores in the 10-100 micron range, for example.

Specimen material in solid, liquid, or gaseous form may be brought into contact with the sample support medium and stored as a sample at discrete sample node 111. In the exemplary embodiment of FIG. 2D, node 111 may swell (as indicted by the dashed lines) as sample material is absorbed by the sample support medium at node 111.

Many examples of sample support media suitable or appropriate for use in conjunction with the FIG. 2D embodiment are commercially available. For instance, open-cell polyurethane foams with high porosity and pores in the 10-100 micron range (such as 30 microns, for example) are generally available and currently used for packaging, padding of small parts or devices, proactive wrappings for injuries, and as precursor material for use in casts.

The sample support medium employed in the FIG. 2D embodiment may display the following properties: compressibility (e.g., to facilitate removal of sample material from the porous structure); rebound ability (i.e., node 111 may return quickly to its original shape when a compressive force is released); an open and porous substructure; capability to absorb water and aqueous buffers; and capability of being cast or cut to fit the containers of a storage element 120 with which carrier 110 is intended to be used. In addition, sample support medium for carrier 110 may include low levels of leaching materials and surfaces which are inert to biological materials. In general, polymeric materials employed at node 111 may be compatible with the reagents used to collect, stabilize, and preserve the sample material, whether that sample material is biological, non-biological, or chemical. Sample support media may also display low levels of particulates and low friability in the wet and dry state.

It will be appreciated that the shape of node 111 illustrated in FIG. 2D is provided by way of example only. While node 111 is depicted as generally circular, other shapes such as squares, rectangles, and other polygons are also contemplated. The general shape and overall dimensions of node 111 may be influenced by some or all of the following factors: the density of the sample support medium; the quantity of sample material to be carried; and the dimensions and capacity of the containers in a storage element 120.

With reference to the various embodiments of sample carrier 110 set forth in detail above, it will be appreciated that magnetic particles or ferromagnetic or ferrimagnetic materials may be implemented at sample node 111, at identification and handling structure 113, or both, to enable magnetic manipulation of sample carrier 110. In some embodiments, for example, magnetic material may be imbedded or otherwise incorporated into, or attached to, node 111, support medium, or identification structure 113.

Figure 2E:
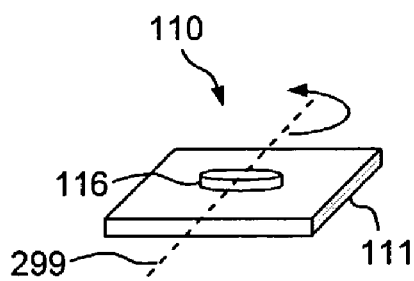
Figure 2F:
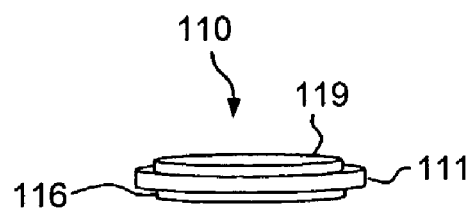

In that regard, FIGS. 2E and 2F are simplified diagrams illustrating embodiments of a sample carrier. Carrier 110 generally comprises a sample node 111 and an integrated or integrally attached magnetic element 116; as indicated in FIG. 2F, carrier 110 may also comprise an identifier 119 such as described in detail above. In the illustrated embodiments, a magnetic field applied from a particular location relative to node 111 may orient sample carrier 110 into an appropriate position to facilitate reading or activating identifier 119 (not shown in FIG. 2E). Further, sample carrier 110 may be handled, translated, or otherwise manipulated using magnetic chucks or other equipment capable of generating a suitable magnetic field.

For example, an applied magnetic field interacting with magnetic element 116 may exert sufficient force to flip or rotate sample carrier 110 about an axis 299 into a desired orientation (as indicated by the curved arrow in FIG. 2E), enabling or facilitating operation of identifier 119. In that regard, magnetic element 116 may be employed in conjunction with a suitable magnetic field to ensure proper alignment of identifier 119 with cooperating instruments such as bar code readers or optical scanners, for example, or with radiant optical energy or RF power sources, antennae, and the like. Additionally or alternatively, magnetic element 116 may allow carrier 110 to be positioned in a desired manner to enable or to facilitate application of specimen material, reagents, preservatives, or other chemicals, for example, to the sample support medium implemented at node 111.

Coated or uncoated magnetic particles or material may be incorporated into sample node 111 or sample support media during manufacture of carrier 110, for example, or following specimen loading. In some such embodiments, node 111 may be produced or manufactured in a magnetic field such that incorporated magnetic material may be arranged or aligned in a desired magnetic orientation or polarization. Alternatively, such magnetic material may be added to the specimen material itself; magnetic material included in the specimen may be bound to sample node 111 with the same or similar chemistry employed to transfer the specimen to node 111.

It will be appreciated from the foregoing that the term "magnetic" in this context generally refers to magnetic, ferromagnetic, or ferrimagnetic properties causing a "magnetic"

material to respond to external magnetic or electromagnetic fields in a predictable manner. Accordingly, in some embodiments, sample carrier 110 may additionally comprise a discrete magnetic element 116 or other magnetic material interspersed throughout the structure of node 111 or other components such that sample carrier 110 may be oriented or otherwise manipulated responsive to an applied magnetic field. A magnetic field may be applied to individual wells, for example, or to an entire storage element in which sample carrier 110 is stored.

Figure 3A:
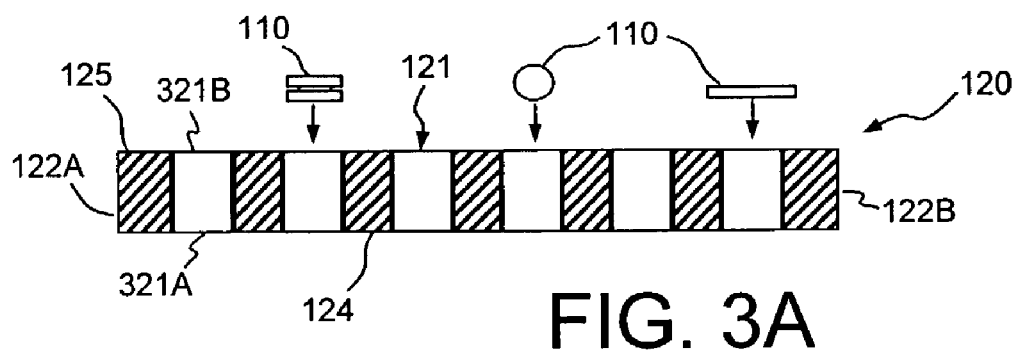
FIG. 3A is a simplified transverse cross-sectional diagram of one embodiment of a storage element taken on the line 3-3 in FIG. 1.

FIG. 3A is a simplified transverse cross-sectional diagram of one embodiment of a storage element taken on the line 3-3 in FIG. 1. As set forth above with reference to FIG. 1B, storage element 120 generally comprises one or more sample containers 121, each configured and operative to receive a sample carrier 110. In the illustrated rectangular embodiment, wells 121 are generally arranged in a predetermined orientation between longitudinal sides 122A-B and transverse sides 123A-B, though storage element 120 may alternatively be generally circular or polygonal in plan.

Carrier 110 and storage element 120 may be constructed and dimensioned such that a sample node is supported in a predetermined spatial relationship relative to specimen material contained in a respective container 121. As represented in FIG. 3A, each carrier 110 may be deposited in a respective container 121 for storage in addition to, or as an alternative to, sample loading; in that regard, storage element 120 may be uniquely configured and operative to accommodate carrier 110 in a clean or sterilized well 121, selectively or optionally to receive specimen material for loading onto node 111, and to seal carrier 110 for archiving. Specifically, the FIG. 3A storage element 120 may be configured and operative to isolate a plurality of sample carriers 110 from each other and to seal off each sample carrier 110 from external contaminants.

In accordance with the FIG. 3A embodiment, each well 121 or specimen container in storage element 120 may generally comprise a reception opening 321B configured and operative to receive a sample carrier 110 and an ejection opening 321A configured and operative in cooperation with an ejector (described below) selectively to eject the sample carrier 110 from well 121. As set forth in more detail below with reference to FIG. 3B, storage element 120 may be sealed, both on first surface 124 as well as on second surface 125.

Figure 3B:
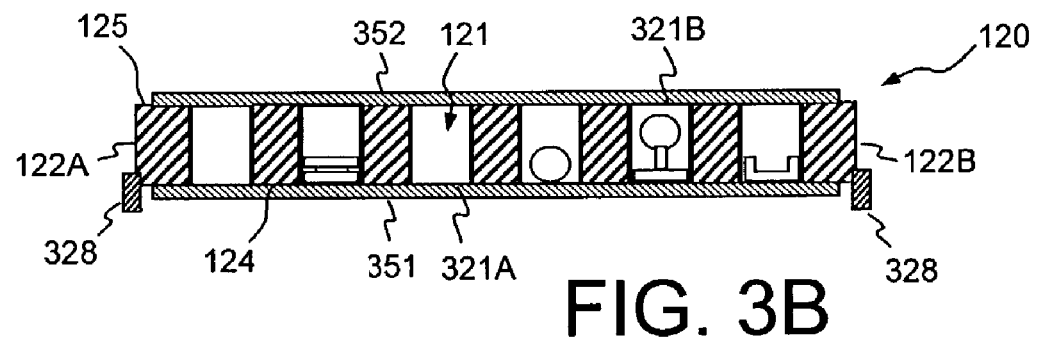
FIG. 3B is a simplified transverse cross-sectional diagram of another embodiment of a storage element taken on the line 3-3 in FIG. 1.

FIG. 3B is a simplified transverse cross-sectional diagram of another embodiment of a storage element taken on the line 3-3 in FIG. 1. As illustrated in FIG. 3B, a first surface 124 of storage element 120 may be closed or sealed, such as by sealing film 351, and a second surface 125 of storage element 120 may be closed or sealed, such as by sealing film 352. Accordingly, each container or well 121 of storage element 120 may be sealed at ejection opening 321A and reception opening 321B by films 351 and 352, respectively, both to secure sample carriers 110 and to prevent entrance of contaminants into wells 121.

In addition to the elements set forth above, the FIG. 3B embodiment of storage element 120 may additionally comprise a lip or skirt 328. In typical applications at archive, research, laboratory, or other facilities, storage elements may be stacked, for example, to optimize available storage space. Attaching or incorporating skirt 328 into the structure of storage element 120 may prevent unnecessary abrasion or degradation of sealing films 351, 352 which may otherwise be caused by contact with surfaces of other storage elements, laboratory benches, and so forth.

In that regard, skirt 328 may be appropriately dimensioned to extend beyond sealing film 351, and may further be sized and configured to engage a surface 125 of an adjacent storage element in a stack while avoiding contact with a sealing film 352 attached to that surface. Skirt 328 may be integral with longitudinal sides 122A-B and may extend in the longitudinal direction along all or only a portion thereof. With reference to the embodiment of storage element 120 illustrated in FIG. 1B, for example, skirt 328 may be implemented as a circumferential component, integrated with or attached to transverse sides 123A-B in addition to longitudinal sides 122A-B. Alternatively, skirt 328 may be implemented as a plurality of posts, guide rails, or other protuberances extending beyond film 351 and situated in selected locations along the periphery (such as at the corners, i.e., junctions of longitudinal sides 122A-B and transverse sides 123A-B) of storage element 120.

Films 351 and 352 may generally be embodied in or comprise various metallic materials, plastics, other polymers, or similar materials such as are typically used for providing thin, flexible sheets or foils employed in sealing articles. In some embodiments, at least one of films 351 and 352 may be constructed of a dielectric substance or other RF transparent material to accommodate any of the various embodiments of a sample carrier 110 employing an RF activated identifier 119 as set forth in detail above. In this context, the terms "radio frequency transparent" and "RF transparent" generally refer to a film of appropriate material and thickness to transmit sufficient RF energy to activate, and to allow operation of, one or more RF transponders as set forth in detail above.

Additionally or alternatively, one or both of films 351 and 352 may be optically transparent, enabling inspection of the contents of well 121, either visually or through use of an optical device; this embodiment may accommodate use of a sample carrier 110 employing a bar code or a light-activated identifier 119. In this context, therefore, the term "optically transparent" generally refers to a film of appropriate material and thickness to allow sufficient light of one or more selected wavelengths to penetrate; i.e., optically transparent films 351, 352 transmit sufficient light to allow visual inspection of sample carriers 110 through the film 351, 352 or to enable trans-film operation of an optical device such as a bar code reader or a light-activated transponder as described above.

It is noted that films 351 and 352 may be pierced during use, allowing a selected sample carrier 110 to be ejected from a specific well 121 as set forth in more detail below with reference to FIGS. 6A-6C. Accordingly, the physical thickness of films 351, 352, for example, as well as the specific properties of the materials selected therefor, may be selectively varied in accordance with system requirements. For example, the shape, material strength, flexibility, and force exerted by a piercing ejector component (described below) may influence some or all of the following: the material selected for films 351, 352; the thickness of films 351, 352; and the techniques employed to apply films 351, 352 to surfaces 124, 125, respectively. In some embodiments, the foregoing factors, inter alia, may be adjusted to ensure that films 351, 352 may be pierced effectively by the selected ejection mechanism.

Various methods of applying films to surfaces are generally known in the art. For example, numerous adhesives and heat sensitive sealing techniques are currently employed in various applications such as pharmaceutical packaging, shrink wrapping, and the like. It is noted that the particular method employed for bonding, adhering, attaching, fusing, or otherwise applying sealing films 351, 352 to surfaces 124, 125 may be influenced by various factors including, but not limited to, the following: material selection and thickness of films 351, 352; material selection, hardness, and surface characteristics of surfaces 124, 125; the intended use of storage element 120 or the sample material maintained therein; and potential chemical interactions (due to either the bonding material or the application technique) with the sample material to be stored in wells 121 of storage element 120. Accordingly, those of skill in the art will appreciate that the method employed to apply sealing film 351 to surface 124 may differ from that employed to apply sealing film 352 to surface 125.

While the present disclosure is not intended to be limited by any specific application or bonding technique, those of skill in the art will appreciate that an appropriate seal between films 351, 352 and surfaces 124, 125, respectively, may prevent contamination of sample carriers 110 disposed in wells 121. Accordingly, in some embodiments, the methods of applying films 351, 352 may be selected to ensure complete bonding around the entire perimeter or periphery of each well 121 at each surface 124, 125; in other words, reception opening 321B and ejection opening 321A of each respective well 121 may be individually sealed and isolated from the adjacent well 121. As an alternative, a simple application technique may adhere or bond a film 351, 352 to a respective surface 124, 125 at only portions or selected areas thereof (e.g., along the perimeter of storage element 120). In this latter embodiment, every individual well 121 may not be isolated from other wells 121 in storage element 120.

As noted above, the methods selected for applying a particular type of sealing film may vary in accordance with the intended use of storage element 120 and the sample material stored in wells 121. Additionally, it will be appreciated that some embodiments may accommodate sealing selected portions of a storage element. By way of example and referring to the storage element 120 depicted in FIG. 1B, each of rows 126 and 127 may be sealed individually as a discrete unit of wells 121.

Figure 4A:
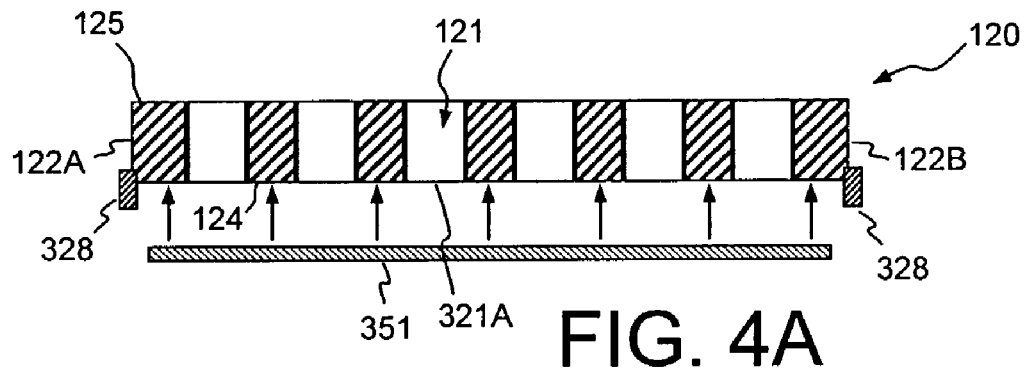
FIGS. 4A-4C represent a series of simplified transverse cross-sectional diagrams of one embodiment of a storage element during use.
Figure 4B:
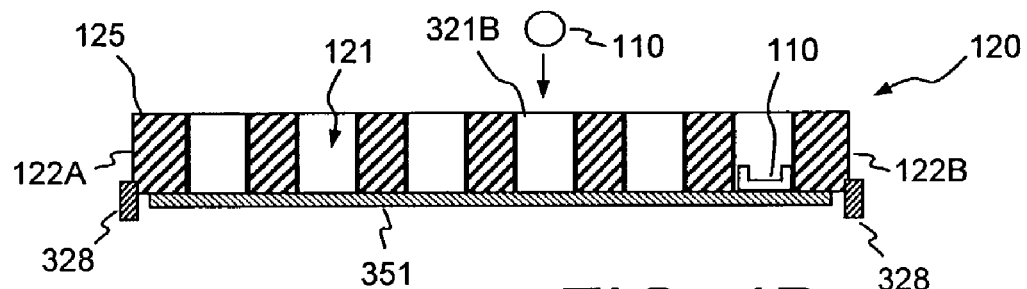
Figure 4C:
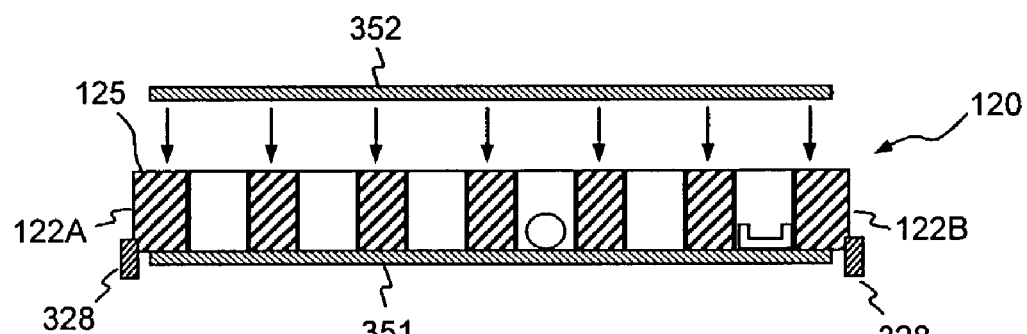

FIGS. 4A-4C represent a series of simplified transverse cross-sectional diagrams of one embodiment of a storage element during use. As indicated in FIG. 4A, a storage element 120 substantially as illustrated and described in detail above may be sealed at a first surface 124 with a sealing film 351, such as a polymeric or metallic film. As set forth above with reference to FIGS. 3A and 3B, film 351 may generally seal an ejection opening 321A for each respective sample container or well 121 in storage element 120. In the FIG. 4A embodiment, the application method employed to attach film 351 may generally bond or adhere film 351 around the perimeter of each ejection opening 321A at surface 124, making each well 121 an independent container. Specifically, film 351 may be bonded to as much of surface 124 as required (e.g., around the periphery of each individual ejection opening 321A) to prevent liquid seepage between wells 121. As set forth above, selected portions of storage element 120 may be sealed in the foregoing manner, depending upon the number of samples to be stored, the sophistication of the apparatus employed to apply sealing film 351 to surface 124, and other factors.

As noted above, each well 121 may include a reception opening 321B configured and operative to receive a sample carrier 110; in that regard, as indicated in FIG. 4B, a sample carrier 110 may be deposited or provided in each respective well 121 of storage element 120. In some embodiments, one or more selectively configured magnetic or electromagnetic fields may be applied to storage element 120, for example, or to individual wells 121, facilitating arrangement or orientation of sample carriers 110 incorporating magnetic elements 116 as set forth above.

As indicated in FIG. 4C, a sealing film 352 may be applied to a second surface 125, simultaneously preventing loss of sample carriers 110 and sealing wells 121 from contamination. Depending upon the intended use of storage element 120 itself, or upon the operational characteristics of the facility with which storage element 120 is intended to be used, film 352 may simply be adhered or otherwise bonded to selected portions of surface 125; alternatively, film 352 may be adhered to surface 125 around the perimeter of each reception opening 321B. In addition to, or as an alternative to, the sealing operation indicated in FIG. 4C, the storage element arrangement depicted in FIG. 4B may be provided with a lid or cover such as may generally be provided for conventional multi-well plates, for example, to prevent introduction of contaminants into wells 121. Specifically, in some implementations, application of sealing film 352 to surface 125 may be omitted in appropriate circumstances, such as, for example, where alternative measures are taken to prevent loss of carriers 110 and contamination of wells 121.

Those of skill in the art will appreciate that specimen material may be loaded onto sample carriers 110 at any time prior to application of film 352, i.e., prior to sealing surface 125. In some embodiments, for example, storage element 120 and its plurality of wells 121 may receive sample carriers 110 pre-loaded with sample material (i.e., already carrying a sample on a sample storage medium) for storage. Alternatively, wells 121 may receive unloaded sample carriers 110; in this embodiment, an appropriate or desired amount of specimen material may be selectively added to wells 121, either before or after sample carriers 110 are deposited therein.

Additionally or alternatively, various primers, denaturants, buffers, solvents, preservatives, or other chemical compounds may be added to wells 121 as desired prior to application of sealing film 352. Where liquid sample material, chemical reagents, or other fluids are introduced to wells 121, film 352 may be bonded or adhered to as much of surface 125 (i.e., around each individual reception opening 321B) as required to prevent spillage, seepage, or other contamination between wells 121.

Figure 5A:
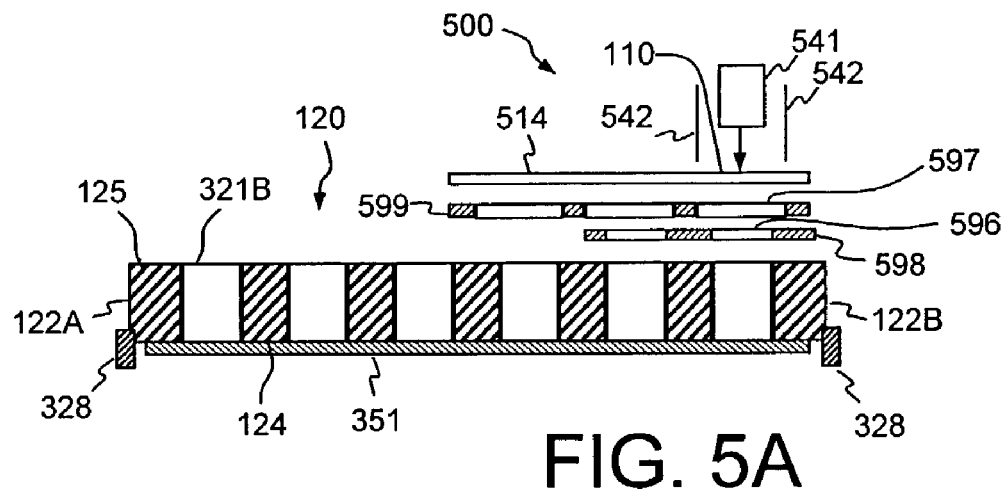
FIGS. 5A-5C represent a series of partially exploded, simplified transverse cross-sectional diagrams of one embodiment of a system configured and operative to insert a sample carrier into a selected container of a storage element.
Figure 5B:
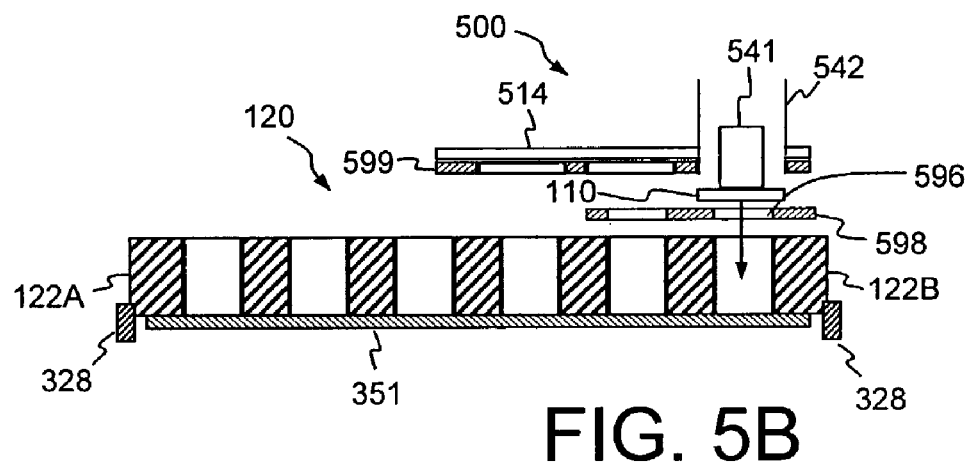
Figure 5C:
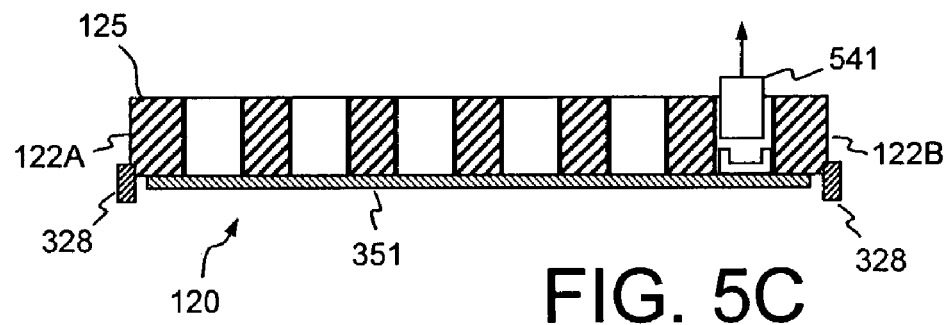

FIGS. 5A-5C represent a series of partially exploded, simplified transverse cross-sectional diagrams of one embodiment of a system configured and operative to insert a sample carrier into a selected container of a storage element. The arrangement of storage element 120 depicted in FIG. 5A is similar to that illustrated and described above with reference to FIG. 4B. A first surface 124 of storage element 120 has been sealed by film 351 at an ejection opening 321A of each respective well 121 substantially as set forth above. In the embodiment illustrated in FIGS. 5A-5C, system 500 generally comprises a layer of substrate 514, a cutting platen or template 599, a retention template 598, a carrier cutting apparatus such as cutter 542, and a plunger 541. The various components of system 500 may be configured and operative to deposit a sample carrier 110 into a respective well 121 of storage element 120 substantially as described below.

As noted above, FIGS. 5A-5C are partially exploded to depict several of the disclosed components more clearly. With respect to the operations described below, it is noted that some embodiments may employ the following initial configuration: retention template 598 may generally be placed in contact with surface 125 of storage element 120 such that a carrier aperture 596 may be aligned with a reception opening 321B of well 121; similarly, cutting template 599 may be placed in contact with retention template 598 such that a cutter aperture 597 may be aligned with carrier aperture 596; finally, substrate 514 may be placed in contact with cutting template 599.

As set forth in detail above, substrate 514 from which sample carrier 110 is cut may comprise or be embodied in any of various cellulose-based filter papers or polymeric material (for example, polyesters, polyacrylics, or polyurethane foam) suitable for binding samples. As noted above, substrate 514 may be placed on or in close proximity to cutting template 599, which in turn is configured and operative to engage or to abut retention template 598. Templates 598, 599 may be constructed of various plastics, metals, ceramics, or other materials sufficiently hard or resilient to withstand forces exerted by cutter 542, plunger 541, substrate 514 and carrier 110, or some combination thereof. It will be appreciated that templates 598, 599 may be integral, i.e., the structural features of each may be incorporated into a single, unitary template. The exemplary illustrations in FIGS. 5A-5C are provided only to facilitate description, and are not intended to be interpreted in any limiting sense.

Cutting template 599 may generally comprise cutter aperture 597 allowing cutter 542, plunger 541, and carrier 110 to pass through cutting template 599 toward retention template 598. In operation, plunger 541 may contact substrate 514 and exert a suitable compressive force; this compressive force may generally place the portion of substrate adjacent aperture 597 in tension, facilitating cutting operations. Cutter 542 may engage substrate 514 and cut a sample carrier 110. By way of example, cutter 542 may be implemented as a borer, an awl, a punch tool, or various other tools, devices, or mechanisms facilitating creation of a plug, chad, or punch-out of substrate 514; numerous mechanisms having such capabilities are generally known in the art. In the FIG. 5A embodiment, cutter 542 may extend through substrate 514 (creating carrier 110) and aperture 597 to ensure a clean, precise cut; accordingly, cutter 542 may make contact with surface 125 of storage element 120 if retention template 598 is not employed.

In FIG. 5A, cutter 542 may be constructed or configured to have similar dimensions as aperture 597; accordingly, carrier 110 may be cut to a selected size and shape in accordance with the various dimensions of cooperating cutter 542 and template 599. In some embodiments, carrier 110 may be cut to have dimensions larger than reception opening 321B of well 121. As most clearly illustrated in FIG. 5B, plunger 541 may continue to advance carrier 110 toward reception opening 321B following the foregoing cutting operation.

Retention template 598 may generally comprise a carrier aperture 596 allowing plunger 541 and sample carrier 110 to pass through reception opening 321B of well 121. Aperture 596 may generally be suitably dimensioned and positioned relative to storage element 120 such that retention template 598 bears and distributes much of the force exerted during insertion of carrier 110 into well 121; additionally or alternatively, retention template 598 may protect surface 125 from cutter 542 extending through aperture 597 of template 599. Accordingly, edges of surface 125 around the periphery of reception opening 321B may be protected from cracking, chipping, denting, or similar damage such as abrasion which may otherwise be caused by the apparatus employed to create and to insert carrier 110 in the embodiment of FIGS. 5A-5C. In that regard, use of retention template 598 may also prevent damage to storage element 120 in cases where carrier 110 has a diameter or other plan dimension greater than that of reception opening 321B.

In some embodiments, for example, retention template 598 may be placed directly on surface 125 during use, and aperture 596 may be precisely dimensioned in accordance with the size and shape of reception opening 321B. In these embodiments, aperture 596 may generally be implemented to have equal or smaller dimensions than reception opening 321B to prevent damage to surface 125 or wells 121. In some cases, however, aperture 596 may be larger than reception opening 321B. In still other embodiments appropriately reconfigured to prevent damage to surface 125, retention template 598 may be optional.

As indicated in FIGS. 5B and 5C, retention template 598 and aperture 596 may facilitate folding of carrier 110 to fit well 121. As plunger 541 proceeds through aperture 596, edges or sides of carrier 110 may be folded or pushed in a predictable manner such as depicted in FIG. 5C. When carrier 110 has been inserted in well 121, plunger 541 may be withdrawn, and the foregoing process repeated for a different carrier 110 and a different well 121.

Where the precise dimensions of storage element 120 as well as the particular size, shape, and spatial arrangement of wells 121 are known, templates 598 and 599 may be fabricated to span the entire surface 125 of storage element 120, i.e., templates 598 and 599 may comprise, for each well 121 in storage element 120 (or a subset thereof), a respective plurality of apertures 596 and 597 arranged in a particular manner to cooperate with the two-dimensional arrangement of wells 121 in storage element 120. This embodiment may enable efficient loading of an entire storage element 120 with sample carriers 110 and may require minimal automated handling or robotic repositioning of templates 598 and 599. Where multiple cutters 542 and plungers 541 are provided in an appropriate arrangement in conjunction with an automated apparatus or robotic system, for example, an entire storage element 120 or large portions thereof (such as a whole row or column of wells 121, for example) may be loaded with sample carriers 110 simultaneously or in a single operation. Alternatively, templates 598 and 599 may be implemented to cut a sample carrier 110 for each individual well 121 sequentially; in this embodiment, for example, relocation or repositioning of templates 598 and 599 from one well 121 to the next may be required.

Those of skill in the art will appreciate that the operations depicted in FIGS. 5A-5C may occur at the stage indicated in FIG. 4B (i.e., after a first surface 124 is sealed, but before a second surface 125 is sealed). Accordingly, the cup shape created for the sample carrier 110 depicted in FIG. 5C may be suitable for addition of liquid sample material, preservatives, or other chemicals into well 121 as set forth above.

FIGS. 6A-6C represent a series of simplified transverse cross-sectional diagrams of one embodiment of a system configured and operative to eject a sample carrier from a storage element. In the exemplary embodiment, system 600 generally comprises an ejector 690 having a piercing tip 691, a feeder/trimmer device 680, and a cartesian coordinate controller 670.

As will become more apparent in the following description, feeder/trimmer 680 may generally comprise a housing 682 operative to accommodate or to maintain a supply of ejector stock (from which ejector 690 may be fashioned, for example), a mechanism (not shown) for advancing the ejector stock from housing 682, and a blade 681 operative to cut the ejector stock at a desired or predetermined location.

In that regard, it will be appreciated that ejector 690 may be embodied in or fabricated from a flexible or semi-rigid rod, wire, or similar elongate stock material. The material selected for the ejector stock may generally be rigid enough to pierce sealing films 351 and 352, but, in some embodiments, soft enough to allow a sharp bias cut for piercing tip 691. Ejector 690 and ejector stock may be constructed of low cost and disposable materials such as metals (e.g., aluminum wire), plastics, or other polymers.

Where the ejector stock is a flexible polymeric or metallic cord or wire, for example, ejector 690 may be cut such that a contaminated portion 699 may be removed while a sterile portion 698 may be retained (as indicated in FIG. 6C and set forth in more detail below). In this embodiment, feeder/trimmer device 680 may feed or supply sterile portion 698 from a spool of ejector stock, for example, either before or after blade 681 cuts ejector 690 separating portions 698 and 699. Various mechanisms and methods embodying the foregoing functionality are generally known. For example, rotary lawn trimming equipment and hand-held or automatic packaging devices are known which employ feeders, to supply flexible or semi-rigid cord from spools or other storage mechanisms, and cutters, operative to cut the cord at a desired location.

In a simplified embodiment, feeder/trimmer 680 may provide an individual (i.e., discrete) or disposable ejector 690 for each ejection operation. For example, housing 682 may comprise one or more racks, quivers, or magazines operative to store a plurality of pre-cut ejectors 690. In such an embodiment, feeder/trimmer 680 may be configured and operative sequentially to position an ejector 690 for use as described below, retract, release, or otherwise dispose of the used ejector 690, and position the next ejector 690 for use in a subsequent ejection procedure. It will be appreciated that the material selected for each ejector 690 need not be flexible in this embodiment.

In operation, coordinate controller 670 may position ejector 690 relative to a particular target well 121 in a given storage element; as depicted in FIG. 1B, the x coordinate may represent the location of well 121 along longitudinal axis 199 of storage element 120, while the z coordinate may represent the distance of well 121 from longitudinal axis 199. Those of skill in the art will appreciate that controller 670 may incorporate various mechanical and electronic components such as sensors, articulated arms, linear or other actuators, servos, and other hardware elements (mechanical, electrical, or electromechanical) configured and operative precisely to position ejector 690 in three dimensional space. Various motion control systems and methods suitable for controller 670 are generally known in the art.

In that regard, controller 670 may include one or more data input ports or communications interface mechanisms configured and operative to receive electronic data or instruction sets enabling or facilitating sample or well 121 identification. In particular, controller 670 may receive coordinate data or other information regarding the location of a specific sample carrier 110; such data may be supplied or provided by, for example, bar code readers, optical or RF transponders, operator input, or other manual or automated devices. As set forth above, laboratory or experimental facilities may employ automated or manual apparatus in conjunction with electronic systems including databases or other data structures, for instance, to catalog and maintain information regarding the identity and location of specific sample material. In accordance with available information, controller 670 may be operative to position ejector 690 at the x,z location of an appropriate well 121 in storage element 120 using various devices and techniques generally known in the art for positioning equipment.

Additionally or alternatively, storage element 120 may be moved or positioned to facilitate alignment of ejector 690 and a target well 121. Various moveable stages or robotic systems, for example, operative independently or in cooperation with hardware implemented at controller 670, are contemplated and currently available. The present disclosure is not intended to be limited by the methods or devices employed to align ejector 690 and well 121, nor by the general constitution of coordinate controller 670 and the specific structural arrangement of components incorporated therein.

Coordinate controller 670 may additionally be operative selectively to advance and to withdraw ejector 690 in the y direction. As indicated in FIGS. 6A-6C, ejector 690 may be advanced in the y direction through a selected target well 121 in storage element 120 and subsequently withdrawn therefrom; in some embodiments, such motion in the y direction may be facilitated or enabled by a linear actuator, for example, operative under control of coordinate controller 670. Additionally or alternatively, some such motion of ejector 690 in the y direction may be provided by feeder/trimmer device 680 as set forth above.

As indicated by the sequence of events depicted in FIGS. 6A and 6B, ejector 690 may pierce film 352, engage sample carrier 110, and eject sample carrier 110 through film 351 into, for instance, a selected well 121B in a daughter plate or other storage element 120B, or into a particular test tube, cuvette, or other container positioned to receive carrier 110 ejected from well 121.

Referring now to FIG. 6C, it will be appreciated that a portion (represented by reference numeral 699) of ejector 690 may be contaminated, or at least may generally be regarded as such, following ejection of carrier 110. Specifically, contact with carrier 110, films 351, 352, and interior surfaces of well 121 may result in traces of sample material or chemicals being deposited on or otherwise attached to portion 699, in whole or in part. Accordingly, portion 699 of ejector 690 may be discarded following the ejection operation to prevent cross-contamination of sample material between carriers 110. In this context, it will be appreciated that portion 699 may generally represent the length of ejector 690 which may potentially come into contact with carrier 110, surfaces of well 121, films 351, 352, or some combination thereof. Specifically, any part of ejector 690 which extends to or beyond film 352, surface 125, or some other selected point during use (and in particular, during the operation depicted in FIG. 6B) may be included in potentially contaminated portion 699.

As indicated in the FIG. 6C embodiment, ejector 690 may be withdrawn from well 121 prior to cutting of portion 699 and subsequent discarding thereof. As an alternative, portion 699 may be cut from the ejector stock prior to withdrawal, i.e., when ejector 690 is in the position indicated in FIG. 6B. This alternative embodiment may ensure that the cut occurs in the correct location along ejector 690 and that the entirety of contaminated portion 699 is removed.

Figure 7:
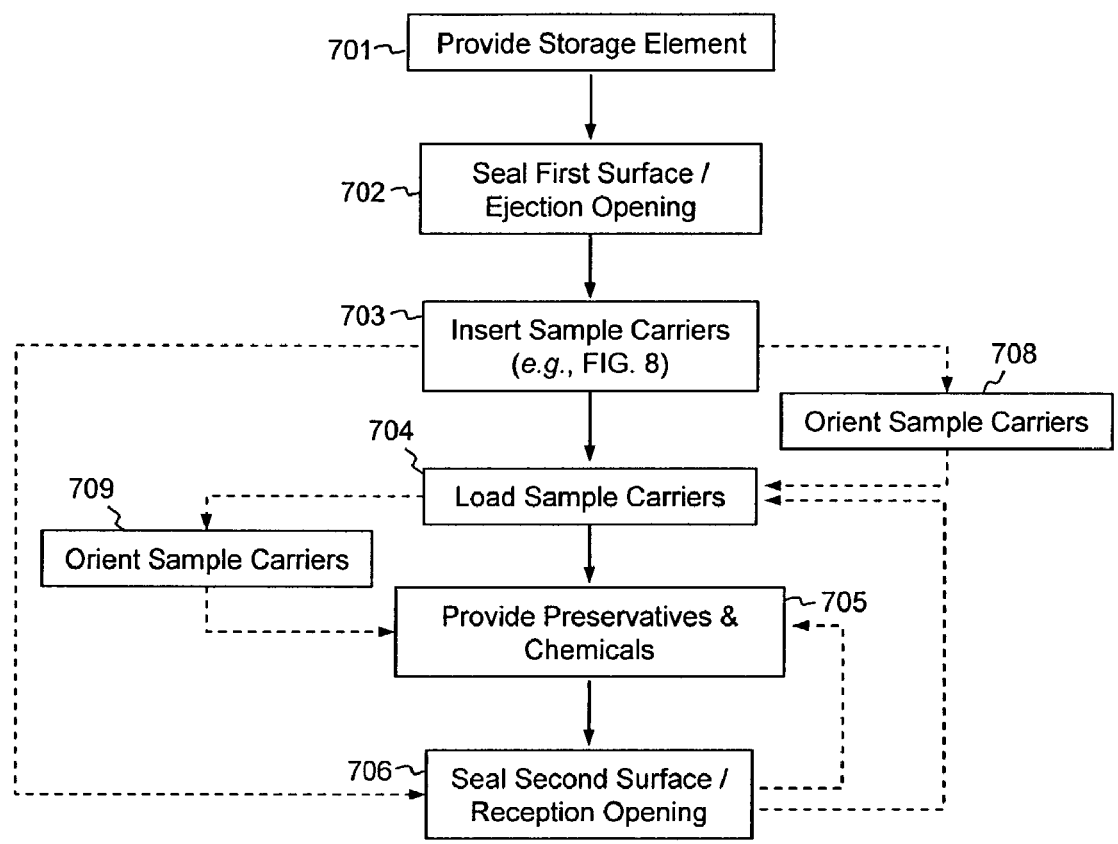
FIG. 7 is a simplified flow diagram illustrating the general operation of one embodiment of a sample archival method.

FIG. 7 is a simplified flow diagram illustrating the general operation of one embodiment of a sample archival method. The sequence depicted in FIG. 7 generally corresponds to the operations illustrated and described in detail above with reference to FIGS. 4A-4C. As indicated at block 701, a storage element substantially as set forth above may be provided. In some embodiments, the storage element may be provided by automated equipment such as robotic handling mechanisms, for example, using machine vision technology operative to read bar codes or other identifying indicia; alternatively, the storage element may be provided by or in cooperation with user or operator input. In this context, "providing" generally refers to identifying a target storage element and placing, orienting, positioning, or otherwise selectively locating the storage element relative to structural components or equipment facilitating or implementing subsequent operations.

As indicated at block 702, a first surface of the storage element may be sealed, for example, with a polymeric or metallic sealing film substantially as set forth above. In particular, a such a film may be bonded or adhered to the first surface around the perimeter of each ejection opening, sealing the ejection opening for each respective sample container or well in the storage element. As set forth above, the entire first surface of the storage element, or only selected portions thereof, may be sealed in the foregoing manner.

As indicated at block 703, a sample carrier may selectively be deposited, provided, or otherwise inserted into each respective well of the storage element. As illustrated and described above with reference to FIG. 4B, each well or container may include a reception opening configured and operative to receive a sample carrier. In some embodiments, the operation depicted at block 703 may comprise the functionality and incorporate some or all of the structural components described above with reference to FIGS. 5A-5C and further illustrated in FIG. 8.

Specimen material may be loaded onto sample carriers as indicated at block 704. In the exemplary FIG. 7 embodiment, an appropriate or desired amount of specimen material may be selectively added to one or more of the wells of the storage element after the sample carriers are deposited therein. As noted above, however, such loading of sample carriers with specimen material may occur at other points in the process. In some embodiments, for example, a storage element and its plurality of wells may receive sample carriers pre-loaded with sample material; specifically, the operation depicted at block 704 may precede any one of the operations depicted at blocks 701-703. Alternatively, specimen material may selectively be added to wells prior to insertion of sample carriers at block 703.

Additionally or alternatively, a desired or predetermined amount of various primers, denaturants, buffers, solvents, preservatives, or other chemical compounds may be selectively added to the wells of the storage element (block 705). As with the carrier loading depicted at block 704, application or provision of preservatives or other chemicals to a sample carrier may be executed at various points in the process. For example, the operation depicted at block 705 may occur prior to one or more of the operations depicted at blocks 703 and 704.

As indicated at block 706, one or more reception openings of a second surface of the storage element may be sealed, for example, with a second polymeric or metallic sealing film, simultaneously preventing loss of sample carriers and preventing contamination of the wells. As set forth above with reference to FIG. 4C, the second film may simply be adhered or otherwise bonded to selected portions of the second surface, or it may be adhered around the perimeter of every reception opening (or a selected subset thereof) in the storage element. Where liquid sample material, chemical reagents, or other fluids are introduced to the wells (such as at blocks 704 or 705, for example), the second film may be bonded or adhered to as much of the second surface as required to prevent spillage, seepage, or other contamination between the wells.

In addition to, or as an alternative to, the sealing operation indicated at block 706, the storage element may be provided with a lid or cover such as may generally be provided for conventional multi-well plates; in some implementations, application of the second sealing film may be omitted.

As noted above, one or more selectively configured magnetic or electromagnetic fields may be applied to the storage element, or to one or more individual wells; such fields may exert appropriate forces facilitating arrangement or orientation of sample carriers incorporating magnetic elements as set forth above. It will be appreciated that other possible orientation techniques and apparatus are contemplated; for example, sample carriers may be oriented or manipulated within the wells mechanically rather than magnetically. As represented at blocks 708 and 709, a method of archiving storage elements as set forth herein contemplates one or more of such orienting operations at various points in the archival process. By way of example, an additional orientation operation may follow the sealing operation depicted at block 706.

Further, it is noted that the sealing operation depicted at block 706 may result in application of a temporary or interim sealing film on the second surface. For example, a temporary seal may prevent contamination of wells or sample carriers prior to loading at block 704 or providing at block 705. As indicated by the dashed arrows in FIG. 7, application of a temporary sealing film may precede loading of sample carriers (block 704) or providing chemicals or preservatives to wells (block 705). In some embodiments, such a temporary seal may be applied prior to any or all of the operations depicted at any of blocks 703-705, for example; it will be appreciated that a temporary sealing film may be subsequently breached or removed, allowing insertion, loading, and preserving of sample carriers as set forth above. An additional or final sealing film may be applied as indicated at block 706 prior to storage or archival of the storage element.

Figure 8:
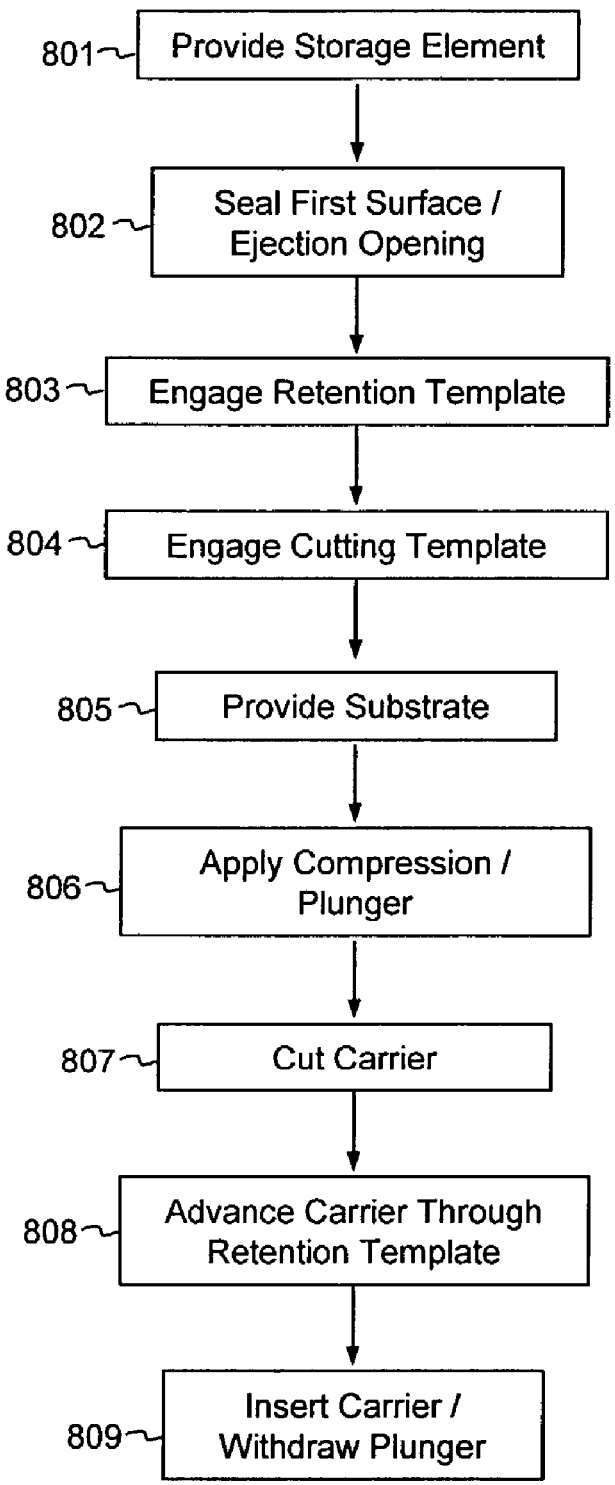
FIG. 8 is a simplified flow diagram illustrating the general operation of one embodiment of a method of inserting a sample carrier into a selected container of a storage element.

FIG. 8 is a simplified flow diagram illustrating the general operation of one embodiment of a method of inserting a sample carrier into a selected container of a storage element. The sequence depicted in FIG. 8 may generally comprise the functionality and incorporate some or all of the structural components illustrated and described in detail above with reference to FIGS. 5A-5C.

As indicated at blocks 801 and 802, a storage element may be provided, and one or more ejection openings in a first surface thereof may be sealed, substantially as set forth above.

As described above with reference to FIGS. 5A and 5B, a retention template may engage (i.e., generally be placed in contact with) the second surface of the storage element such that a carrier aperture in the retention template is aligned with a reception opening of a well (block 803). Similarly, a cutting template may engage or be placed in contact with the retention template such that a cutter aperture in the cutting template is aligned with the carrier aperture (block 804). A substrate, from which a sample carrier may be cut and generally comprising any of the various sample support media set forth above, may be provided in contact with the cutting template (block 805).

Where the precise dimensions of the storage element (and in particular, the size, shape, and spatial arrangement of the wells) are known, the templates may be configured and operative to span the entire second surface of the storage element to facilitate efficient loading of an entire storage element with sample carriers. Where multiple cutters and plungers are provided in an appropriate arrangement in conjunction with an automated apparatus or robotic system, for example, an entire storage element, or portions thereof, may be loaded with sample carriers simultaneously or in a single operation. In other words, for every well in the storage element, or for a selected subset thereof, some or all of the operations depicted at blocks 806-809 and described below may occur in parallel.

A compressive force may be applied by a plunger, for example, or similar tool as indicated at block 806. A sample carrier, having dimensions dictated or influenced by the cutting template, for example, may be cut from the substrate as indicated at block 807. As illustrated in the FIG. 5A embodiment, for example, the cutter may extend through the substrate and the cutting aperture to ensure a clean, precise cut. It will be appreciated that the order of operations depicted at blocks 806 and 807 may selectively be reversed, for instance; alternatively, compression and cutting may occur substantially simultaneously.

As noted above, the sample carrier may be cut to a selected size and shape in accordance with the various dimensions of a cooperating cutter and the cutting template. As indicated at blocks 808 and 809, respectively, the plunger or other tool may advance the sample carrier through the carrier aperture in the retention template and into the well following the foregoing cutting operation. In that regard, the carrier aperture may generally be suitably dimensioned and positioned relative to the storage element such that the retention template bears and distributes much of the force exerted during insertion of the carrier at block 809. When the carrier has been inserted, the plunger may be withdrawn, and the foregoing process repeated for a different carrier and a different well.

Figure 9:
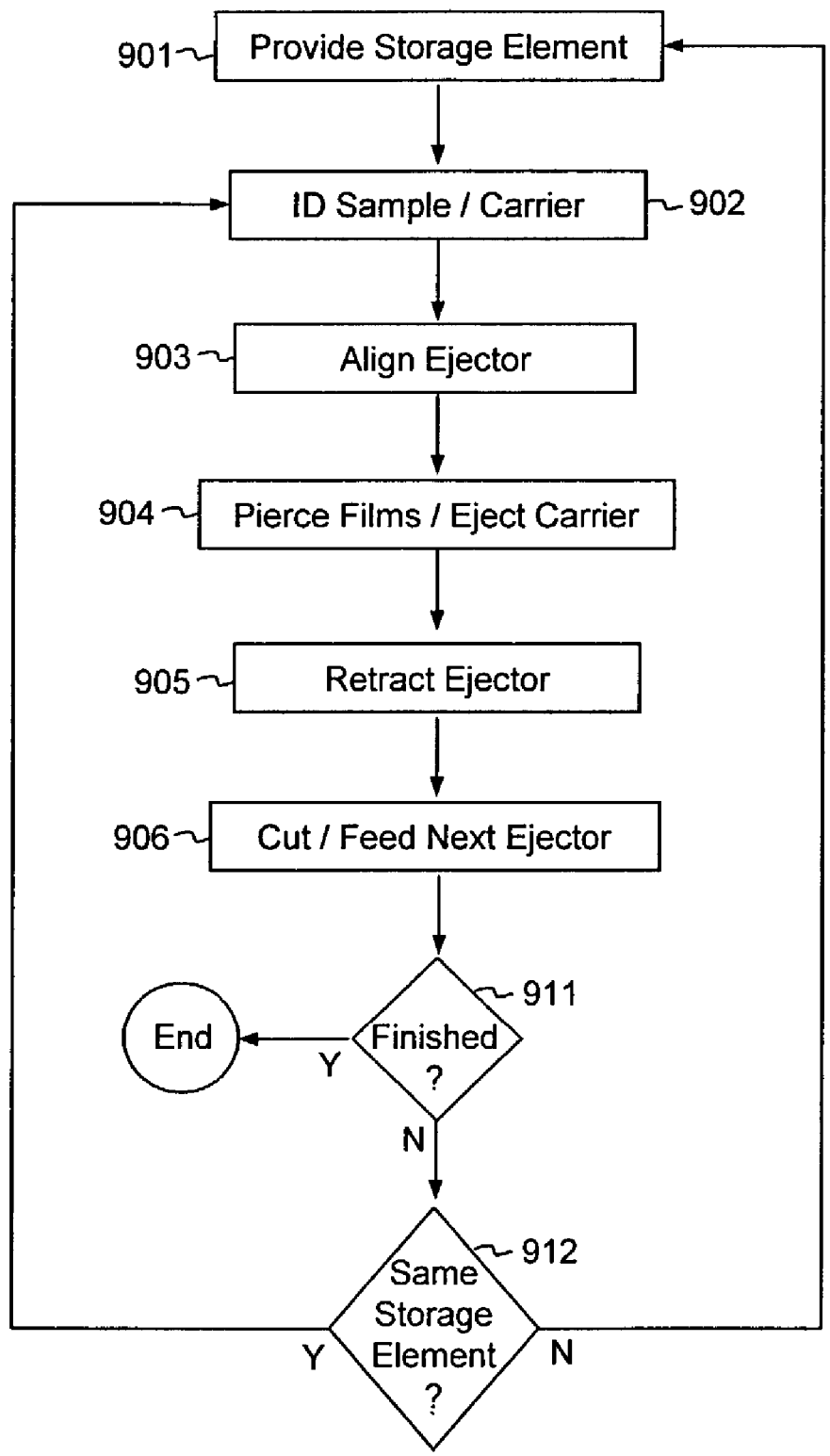
FIG. 9 is a simplified flow diagram illustrating the general operation of one embodiment of a method of ejecting a sample carrier from a storage element.

FIG. 9 is a simplified flow diagram illustrating the general operation of one embodiment of a method of ejecting a sample carrier from a storage element. The order of operations depicted in FIG. 9 generally corresponds to the sequence of events illustrated and described in detail above with reference to FIGS. 6A-6C.

A storage element in which a target sample is archived may be provided as indicated at block 901. This providing may comprise any of the various forms of manual or automated identification, handling, manipulation, and placement set forth in detail above.

As indicated at block 902, a target sample or carrier archived or maintained in the storage element may be identified. In this context, "identifying" a target sample or carrier generally comprises locating that target sample or carrier within the storage element provided at block 901, i.e., ascertaining the location of one or more particular wells or sample contains in which a suitable target sample is archived. By way of example, such identifying may be facilitated by some or all of the following, without limitation: data records comprising sample information and maintained in a database or other computer readable medium; data supplied or provided by, for example, bar code readers, optical or RF transponders, or other manual or automated devices; user or operator input; or any combination of the foregoing.

As set forth above, laboratory or experimental facilities may employ automated or manual apparatus in conjunction with electronic systems including databases or other data structures, for instance, to catalog and maintain information regarding the identity and location of specific sample material. The operations at blocks 901 and 902 may make extensive or limited use of such equipment.

An ejector such as illustrated and described in detail above may be aligned with a well containing the target sample (block 903), either subsequent to, or in conjunction (i.e., substantially simultaneously) with, the identifying at block 902. The alignment at block 903 may be executed manually in some systems, for example, or facilitated by automated equipment such as precision stepper motors, articulated arms, cartesian coordinate controllers, and the like as set forth above.

The ejector may be advanced through the target well, piercing sealing films and ejecting the sample carrier (block 904) substantially as described above with reference to FIGS. 6A-6B. As noted above with reference to FIGS. 6B and 6C, the ejector may be retracted from the target well (block 905) prior to cutting and discarding a potentially contaminated portion (block 906). As indicated at block 906, a new ejector may be supplied or fed, or a sterile portion of the ejector stock may be exposed, for subsequent sample carrier ejection operations.

Where no further samples are desired as determined at the decision block 911, the sequence may end and the storage element may be returned to the sample archive or other location in a laboratory facility. Where one or more additional samples are required, an additional determination may be executed at decision block 912. If a new target sample or carrier is archived within the storage element already in use, the operation may loop back to block 902 for identifying and locating a well maintaining the selected sample. If, on the other hand, a new target sample is not archived within the storage element currently in use, that storage element may be returned to the archive, and control of the operation may loop back to block 901 for identifying and providing a storage element containing the selected target sample.

Returning now to FIGS. 2A-2F, it will be appreciated that the sample support medium selected for node 111 may be influenced by the type of sample material to be stored and the overall functionality of the archive or laboratory facility in which the sample material will be used. When an appropriate sample support medium (polyurethane foam, for instance) has been selected, the medium may be compressed and exposed to a DNA stabilizing solution such as sodium dodecylsulfate (SDS), guanidinium salts such as the hydrochloric acid (HCl) salt, uric acid, and sodium Ethylenediamine Tetraacetic Acid (EDTA). Compressing the sample support medium and allowing the liquid to be drawn up into the porous structure (similar to a sponge soaking up water) may facilitate absorption of the solution. Alternatively the sample support medium may be obtained in the dry, compressed form and allowed to soak up the liquid, swelling as it wets.

After imbibing the solution with the dissolved reagents, the sample support medium may be air dried or, if the reagents are in sufficiently high concentration, the medium may be squeezed dry and then air dried. Alternatively, the medium may be dried with hot air (such as in an oven or kiln), or in a vacuum. After drying, the medium may generally retain a coating of the reagents sufficient to lyse cells, rupture nuclear membranes, inactivate pathogens, and, importantly, to protect and archive biological nucleic acid samples. Subsequent to the foregoing preparation technique, the medium may be retained as a roll or a sheet, for example, or may be cut into any shape desirable for appropriate sample storage. The medium may also be dried under compression to provide a thin, wafer-like unit that will swell and absorb liquid sample material as it is placed in contact with the liquid (e.g., as indicated in FIG. 2D).

When a sample is desired for further analysis or other use, a node 111 comprising a sample support medium as indicated in FIG. 2D may be removed from storage and placed in a suitable container. If the sample originally loaded onto node 111 were purified, then the sample material may be easily recovered. In some embodiments, node 111 may be re-wet, for example, with distilled water or a suitable buffer; node 111 may then be treated with an appropriate chemical or solution (and heat, if suitable or required, depending upon, for example, other chemical factors), causing the sample support medium at node 111 to release the sample material into solution; finally, the solution containing the sample material may be withdrawn from the container.

In the FIG. 2D embodiment, suitable withdrawal methods may include some or all of the following techniques: compressing the storage medium at node 111 to squeeze out the solution for withdrawal by pipette; centrifuging the storage medium at node 111 in a spin basket or in a multi-well filter plate to force the liquid out of the porous structure; or other known methodologies having utility in separating fluids from flexible porous media.

If the sample originally loaded onto node 111 were an impure nucleic acid or mixture of biological materials (e.g., whole blood, DNA, cell culture media, blood plasma, or the like), then further purification may be desirable. In some embodiments accommodating such further purification, several wash steps may be implemented such that node 111 may be washed or rinsed with water or buffer to remove impurities prior to recovery of purified sample material.

Following are specific examples demonstrating the utility of the various described embodiments.

Example 1

Archiving Blood Plasma

A quantity (approximately 500 microliters) of blood plasma is added to the FIG. 2D embodiment of a sample carrier node. In this example, the node has a 1 cm diameter and a thickness of 0.1 cm. The node is constructed of polyurethane foam with an average pore dimension of 30 microns and a porosity of 92%. The node has been pre-treated with a mixture of 2% sodium EDTA, 4% TRIS, and 1% uric acid and dried in the compressed state. Liquid sample material (blood plasma) is added slowly as the node swells to a thickness of 0.5 cm (1 cm diameter remains unchanged). Upon completion of swelling, the sample node is placed in a vacuum oven at 40 degrees Celsius and allowed to dry. The dried node is then transferred to a suitable storage element (such as a standard 96-well plate, for example) and a heat-applied sealing film is affixed to seal the plate openings (i.e., the reception openings in this example). The storage element is then placed in a clean, dry area for long term storage.

Example 2

Recovery of Retrieved Blood Plasma Archive Sample

When the sample material is required for further study, the sample node of Example 1 is retrieved from storage and transferred from the storage element or plate into a daughter plate or other suitable container. If reconstituted plasma is the desired product, 400 microliters of de-ionized, sterile, filtered water is added to the container and allowed to re-wet the node for five minutes. A plunger or rod is then used repeatedly to compress and to release the node—the node may be compressed and released ten times or more to ensure good mixing of the water and the stored biological materials. After a final compression, the liquid is collected and saved for analysis as reconstituted blood plasma. Alternatively, the re-wet node may be placed into one well of a multi-well filter plate or in the spin basket of a centrifuge filter; accordingly, the centrifuge (rather than the plunger method) may be used to recover the liquid.

Example 3

Archiving of Whole Blood

Same as Example 1, except 4% SDS is added to the mixture to lyse the cells and nuclei and to free the DNA for storage.

Example 4

Purification of Retrieved DNA from Blood Sample

Same as Example 2, but the node is re-wet with TE buffer and rinsed twice with TE buffer using similar techniques for liquid removal; subsequently, the node is heated to 85 degrees Celsius for five minutes in 400 microliters of de-ionized, sterile, filtered water. Recovery of the sample material may be done using either compression or centrifugation.

Examples 5 and 6

Automated Recovery of Samples

Same as Examples 2 and 4, except the multi-well plates are placed on a Tecan Robotic Liquid Handler. The Tecan apparatus then automatically adds the liquid as required. In addition, the liquid handler can be used to pick up a disposable plunger (similar to a blunt tipped disposable pipette tip) to compress and release the node. Addition of a robotic arm leading to a centrifuge allows the recovery of the sample in a second (collection) plate after processing.

Figure 10A:
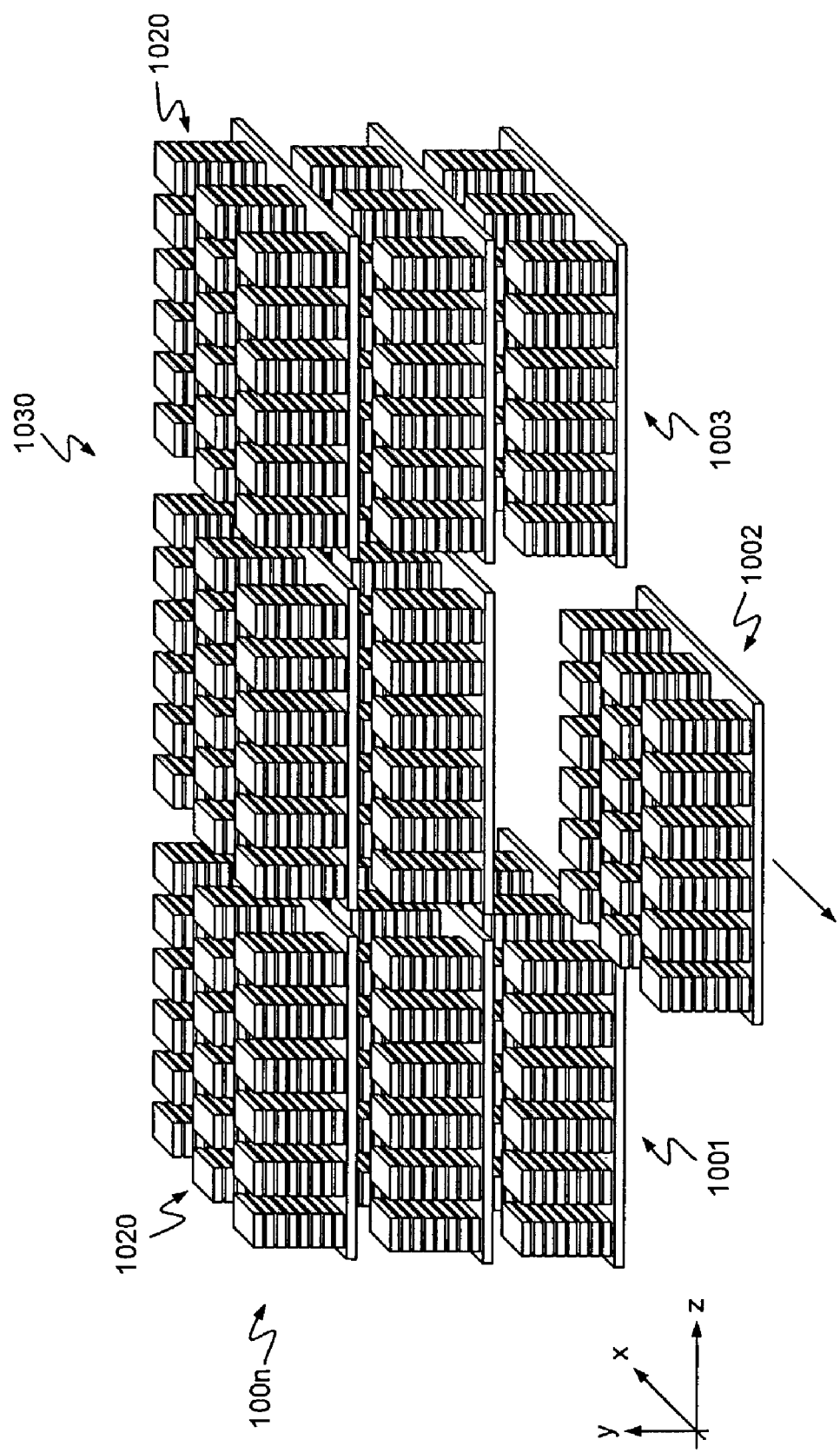
FIG. 10A is a simplified perspective diagram of one embodiment of a sample storage component configured and operative for use in an archive facility.
Figure 10B:
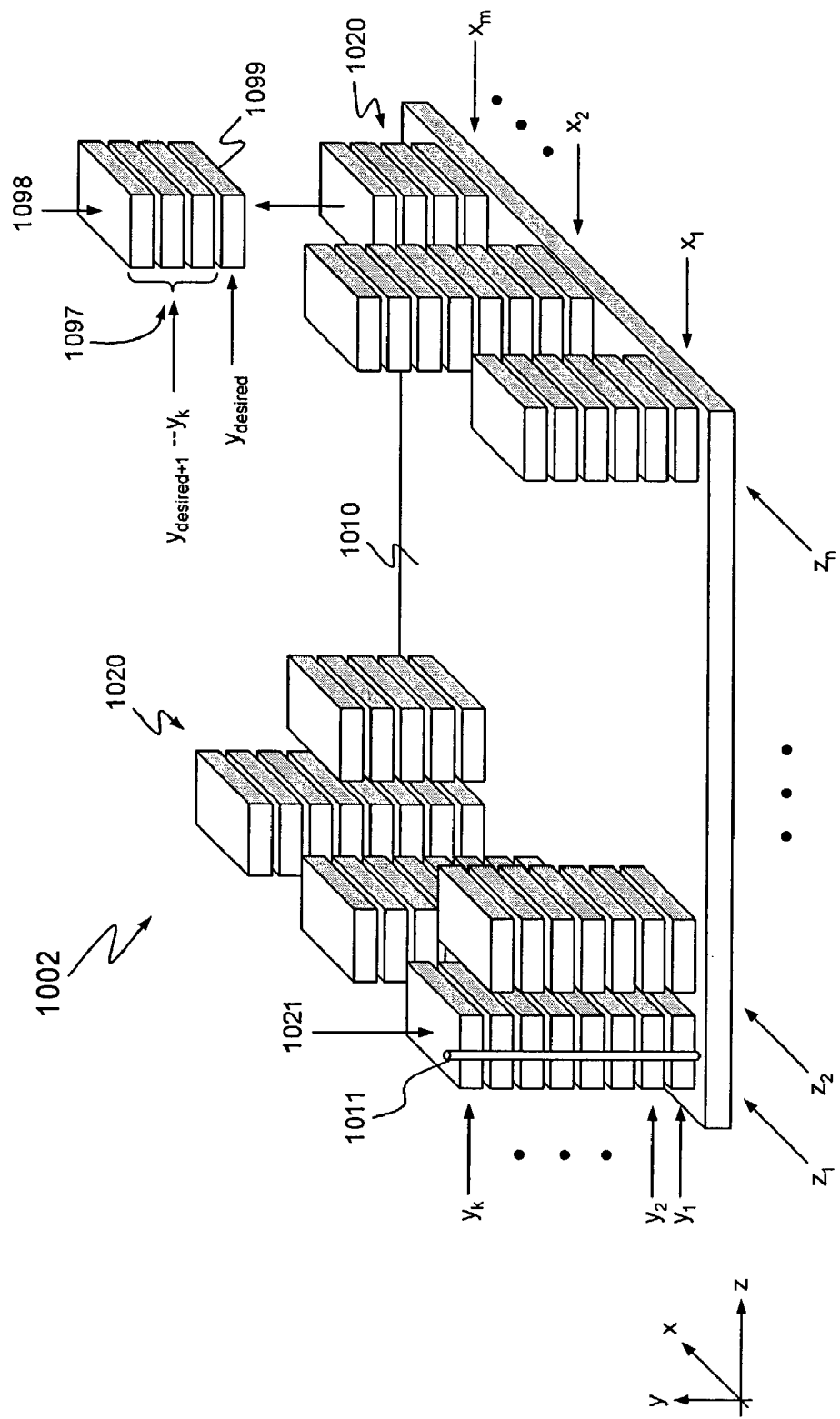
FIG. 10B is a simplified perspective diagram illustrating one embodiment of a receptacle configured and operative for use in conjunction with a sample storage component.

Returning now to the drawing figures, FIG. 10A is a simplified perspective diagram of one embodiment of a sample storage component configured and operative for use in an archive facility, and FIG. 10B is a simplified perspective diagram illustrating one embodiment of a receptacle configured and operative for use in conjunction with a sample storage component. As represented in FIG. 10A, sample storage component 1032 generally comprises a plurality of receptacles 1001-100$n$ arranged in a desired three dimensional geometry or configuration. It is noted that the present disclosure is not intended to be limited by the particular arrangement illustrated in FIG. 10A; those of skill in the art will appreciate that sample storage 1032 may further comprise any number of additional receptacles 1001-100$n$ in any of the x, y, or z directions without inventive faculty.

Each receptacle 1001-100$n$ may be embodied in a movable drawer, tray, shelf, rack, or equivalent structure suitable for supporting or containing one or more storage elements (reference numeral 1020) such as set forth in detail above. As indicated in FIG. 10A, receptacles 1001-100$n$ may be movable relative to each other, enabling access to storage elements 1020 contained in or disposed on each respective receptacle 1001-100$n$; such access may be via manual or robotic handling mechanisms (not shown), depending upon, among other things, the sophistication of the various hardware and software components of the archive facility in which sample storage 1032 is implemented.

For example, receptacles 1001-100$n$ may be operatively engaged with rollers, bearings, rails, tracks, and the like, as is generally known in the art. In such an embodiment, receptacle 1002 may be translated in the x direction as indicated in FIG. 10A, allowing placement, retrieval, or other manipulation of one or more storage elements 1020 as set forth in more detail below.

In accordance with the FIG. 10B embodiment, receptacle 1002 generally comprises a support surface 1010 operative to carry, support, or otherwise to engage a plurality of storage elements 1020 in a two dimensional configuration comprising one or more stacks (such as indicated by reference numeral 1021) of storage elements 1020. Accordingly, storage elements 1020 may be arranged in a three dimensional configuration substantially as shown; as noted above with respect to receptacles 1001-100$n$, the specific arrangement, configuration, number, or spatial interrelation of stacks 1021 or storage elements 1020 may vary in accordance with system requirements, capabilities and limitations of robotic handling apparatus or systems, the size and shape of storage elements 1020 or receptacle 1002, and so forth. The rectangular embodiment of FIG. 10B is shown and described for simplicity, by way of example only, and not by way of limitation.

In some embodiments, a desired number, k, storage elements 1020 may be stacked in the y direction. It will be appreciated that each stack 1021 in any given receptacle 1002 may maintain a different number of storage elements 1020. Each storage element 1020 in a given stack 1021 may be secured or maintained in place, for example, with a series of orienting posts or integral interlocking features associated with each storage element 1020. For example, each storage element 1020 may be provided with one or more alignment prongs, protuberances, or skirts designed and operative to engage one or more corresponding slots, grooves, or notches in neighboring storage elements 1020 when one or more storage elements 1020 are stacked. Various methods of providing interlocking structural features operative to stabilize items when stacked are generally known in the art; in some embodiments, for example, each storage element 1020 may comprise a skirt or flange operative to engage the top surface of an underlying storage element 1020 as set forth in detail above with reference to FIG. 3B. Specifically, such interlocking structural features generally prevent movement of one storage element 1020 in a given stack 1021 relative to the others in the same stack 1021; movement in the y direction allows interlocking structural features to disengage, enabling subsequent movement of storage element 1020 in the x or z directions. Additionally, as noted above, such interlocking structural features may prevent damage or wear to films deposited or adhered to surfaces of storage elements 1020.

Additionally or alternatively, one or more guide posts, rails, or similar stabilizing structures extending in the y direction from support surface 1010 may facilitate stabilization of each stack 1021 and prevent movement of storage elements 1020 relative to each other or relative to support surface 1010. In some embodiments, each storage element 1020 may be constructed and operative to engage such a stabilizing structure. In the FIG. 10B embodiment, for example, a stabilizing structure 1011 is illustrated as a post extending from support surface 1010. In operation, storage elements 1020 may include a notch or depression dimensioned to engage or to abut stabilizing structure 1011 such that relative movement (in either the x or z direction) of storage elements 1020 in stack 1021 is prevented.

In the foregoing or an equivalent manner, the k storage elements 1020 in any given stack 1021 may be prevented from slipping, i.e., relative movement in either the x or z direction may be prevented. Additionally, in such an embodiment, one or more edges (oriented along the x or z axes) of the stacked storage elements 1020 may be accessible by appropriate handling mechanisms.

A plurality of stacks 1021 may be stored or maintained in receptacle 1002, and may generally be arranged on support surface 1010 as a two dimensional configuration with a maximum dimension of n stacks (in the z direction) by m stacks (in the x direction), as depicted in FIGS. 10A and 10B. Spacing between the various stacks on support surface 1010 may generally be a function of the size and pattern of any stabilizing structure 1011 (embodied as a post or guide rail, for example) extending in the y direction from support surface 1010, and the clearance required for tooling or handling apparatus to select and to engage a single stack 1021 in receptacle 1002. In the exemplary embodiment, therefore, a receptacle 1002 accommodating a three dimensional configuration of stacked storage elements 1020 has a maximum capacity of n×m×k storage elements 1020.

In operation, receptacle 1002 may be manipulated (e.g., such as indicated in FIG. 10A), in such a manner as to allow access to each storage element 1020 in the configuration arranged on support surface 1010. In particular, each storage element 1020 in each stack 1021 may be individually addressable in terms of x, y, and z coordinates, for example, enabling easy identification and direct access to every addressable storage element 1020. In some embodiments, storage elements 1020 may be accessed by a robotic arm or other automated handling apparatus for placement, retrieval, or manipulation substantially as set forth below.

One or more handling apparatus, robotic arms, or other mechanical devices may retrieve any storage element 1020 from any given stack 1021 in receptacle 1002; in FIG. 10B, for example, a target storage element 1099 is illustrated as positioned in a stack 1098 (at location $x=x_m$, $z=z_n$) at a desired y coordinate ($y=y_{desired}$). In the exemplary embodiment, the handling apparatus or robot arm may extract target storage element 1099 from stack 1098. First, the handling apparatus may grasp and lift all storage elements from the top (i.e., $y=y_k$) of stack 1098 down to and including target storage element 1099 at $y=y_{desired}$. Both storage element 1099 and the upper portion 1097 (i.e., at $y=y_{desired+1}$ through $y_k$) of stack 1098 may be manipulated as a unit. In accordance with such an embodiment, target storage element 1099 as well as storage elements in upper portion 1097 of stack 1098 may be collectively translated to a desired position in an archive facility; storage element 1099 may then be placed in an appropriate location. At a specified, predetermined, or dynamically selected position, for example, the handling apparatus may release target storage element 1099 while retaining the remaining storage elements in upper portion 1097 of stack 1098.

The remaining upper storage elements corresponding to $y=y_{desired+1}$ through $y_k$ may be returned to the configuration at receptacle 1002, either at the original stack location ($x=x_m$, $z=z_n$) or at some other more convenient location within the available n×m×k volume of receptacle 1002. In the former case, for example, the resulting stack at $x=x_m$, $z=z_n$ may only contain k−1 storage elements 1020 following this sequence. Alternatively, the remaining upper storage elements may be repositioned at another receptacle (1001 or 1003-40n in FIG. 10A), for example.

The foregoing storage arrangement and retrieval technique generally provide space-efficient, high-density storage in which individually addressable and directly accessible storage elements 1020 may occupy most of the available volume in a sample storage component 1032 of a storage facility. A suitable data model for representing the respective locations (i.e., individual addresses in three dimensional space) of each storage element 1020 in sample storage 1032, however, must be more complex than typical data models employed in conjunction with conventional systems. For example, within a given stack 1098, removal and insertion operations affect not only the position of the target storage element 1099, but also all of those storage elements above it, i.e. those in locations $y=y_{desired+1}$ through $y_k$.

An appropriate data model for the FIG. 10A sample storage component 1032 may represent each possible storage location, including unoccupied potential locations, as one or more records in a table, database, or other suitable data structure, for instance, which may be maintained at data storage medium as described above. In some embodiments, such a table or database may include one record for each location, where each record may include, inter alia, the following fields:

receptacle identification (e.g. 1002);
row identification (i.e. x coordinate);
column identification (i.e. z coordinate);
stack position identification (i.e. y coordinate);
storage element identification (e.g. 1099); and
state (e.g. occupied, empty, reserved).

The receptacle, row, and column fields may, in combination, specify or uniquely identify a particular stack (such as 1098 in FIG. 10B) within the entirety of the volume of sample storage 1032. The stack position field may enable identification of the desired height, or y coordinate, of a selected storage element within the targeted stack. Additionally or alternatively, the storage element identification field, if present, may indicate or uniquely identify a particular storage element in a given storage location. Further, the state field may indicate whether a particular location is empty or full.

Accordingly, each storage element 1020 may be individually addressable in three dimensional space using appropriate references to receptacle identification and coordinate axes. In some storage strategies such as described below in detail with reference to FIG. 10C, for example, each storage element 1020 may be individually addressable in terms of two dimensional coordinates within a given receptacle. In the FIG. 10B storage strategy embodiment, three coordinates (in addition to a proper receptacle identification) may be required for accurate addressing of each individual storage element 1020.

Those of skill in the art will appreciate that some embodiments may dynamically cross-reference the storage element identification field with receptacle identification and x, y, and z coordinate information; accordingly, the storage element identification field may be sufficient to enable a robotic device to ascertain the address of any given storage element in three dimensional space and to retrieve that particular storage element. The storage element identification field may correspond to, or work in conjunction with, the bar code identification tags described in the related applications, for example, and may uniquely identify each storage element, as well as the samples contained therein.

In an alternative embodiment, storage elements 1020 or stacks may be stored or archived "on end" in receptacles 1001-100n. In the embodiment illustrated in FIGS. 10A and 10B, for example, "on end" generally refers to a rotation through a full 90 degrees on either the x axis, the z axis, or both, such that storage elements 1020 are not stacked on support 1010. It will be appreciated that this alternative storage methodology may simultaneously provide high storage density as well as rapid and efficient access to storage elements.

Figure 10C:
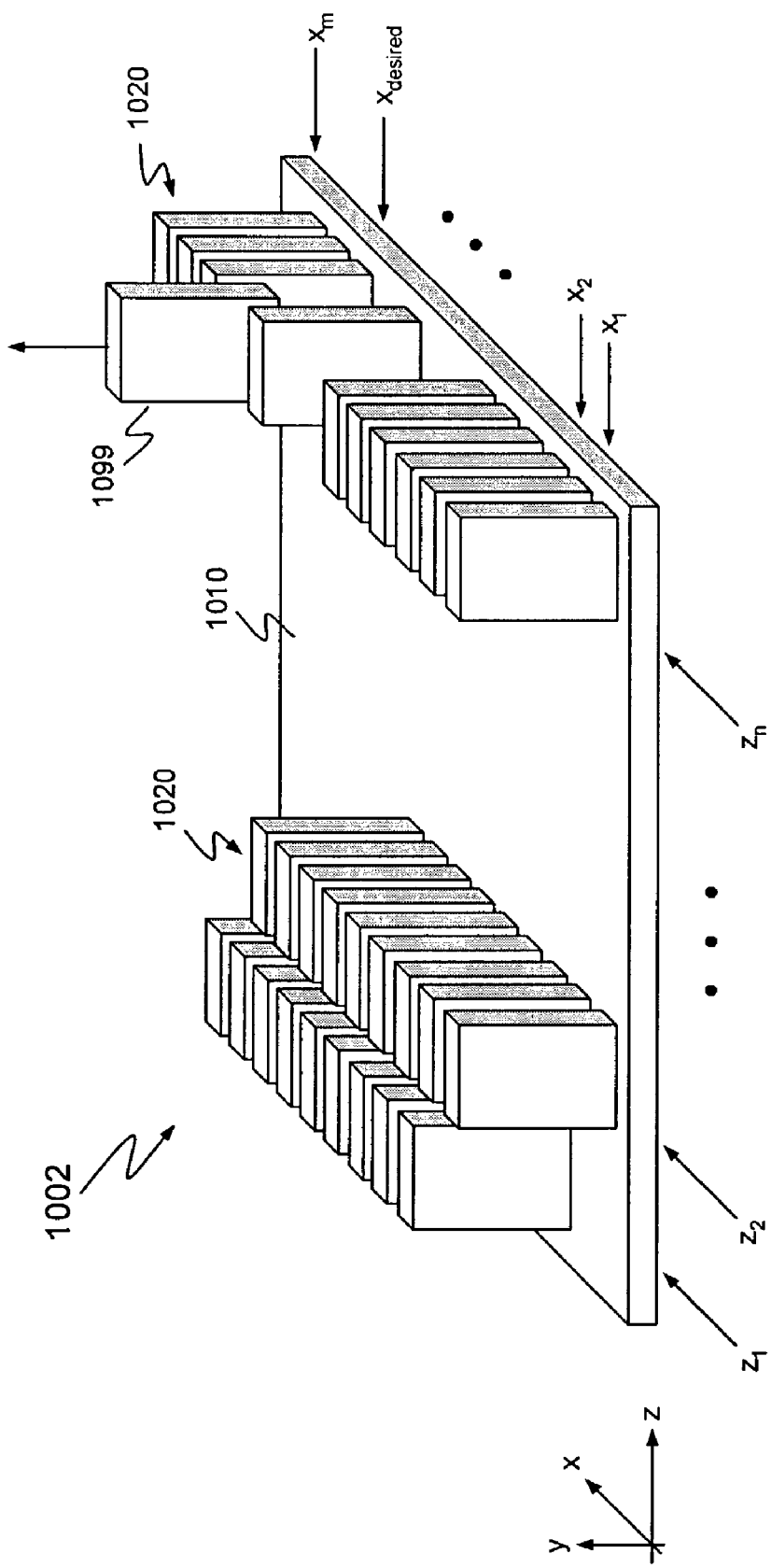
FIG. 10C is a simplified perspective diagram illustrating another embodiment of a receptacle configured and operative for use in conjunction with a sample storage component.

FIG. 10C is a simplified perspective diagram illustrating such an alternative embodiment of a receptacle configured and operative for use in conjunction with a sample storage component. As noted above, storage elements 1020 may be stored on end in receptacle 1002; in the exemplary FIG. 10C embodiment, storage elements 1020 have been rotated 90 degrees on the z axis relative to their orientation in FIGS. 10A and 10B. Additionally or alternatively, storage elements 1020 may be rotated on the x axis, depending upon, for example, the size and shape of receptacle 1002, the size, general operability and clearance requirements of handling mechanisms, and the like.

It will be appreciated that orienting storage elements 1020 on end as illustrated in FIG. 4C may introduce additional requirements related to preventing loss of sample material. Accordingly, each storage element 1020 in the FIG. 10C embodiment may be sealed, for example, as set forth in detail above with reference to FIGS. 4A-4C; alternatively, storage elements 1020 may contain only sample material that will stay in place when its respective storage element 1020 is rotated.

The FIG. 10C strategy of archival and retrieval may provide superior storage density for a given storage element pitch in a particular receptacle. In addition, since storage elements 1020 are not arranged in stacks, every storage element 1020 may be retrieved directly (i.e., any given storage address or location may be accessed without disturbing a storage element 1020 present at any other address), allowing a simple data model. For example, a target storage element 1099 may be simply addressed using only x and z coordinates; as depicted in FIG. 10C, target storage element 1099 is located at $x=x_{desired}$ and $z=z_n$. These two coordinates, along with a receptacle identification field, may be sufficient to locate any given storage element 1020 within the entire three dimensional space encompassed by sample storage component 1032.

As with the embodiment illustrated in FIGS. 10A and 10B, at least one edge (oriented along the x or z axes in FIG. 10C) of every storage element 1020 is exposed in an arrangement such as depicted in FIG. 10C; accordingly, an identifying label or other indicia (such as represented by reference numeral 129 in FIG. 1B, for example) may be scanned by manual or robotic handling mechanisms. It will be appreciated that a suitable handling apparatus may include appropriate hinges, gimbals, or other mechanisms enabling rotation or revolution about selected axes; in this embodiment, a single handling apparatus may be suitable for different storage strategies (exemplified in FIGS. 10B and 10C, for example) employed at different receptacles.

The present invention has been illustrated and described in detail with reference to particular embodiments by way of example only, and not by way of limitation. Those of skill in the art will appreciate that various modifications to the exemplary embodiments are within the scope and contemplation of the present disclosure. Therefore, it is intended that the invention be considered as limited only by the scope of the appended claims.

What is claimed is:

1. A method of retrieving an archived biological sample, comprising:
    aligning an ejector with a container in a storage system, wherein said container comprises:
        a reception opening and an ejection opening,
        a first film sealing the ejection opening of said container; and
        a sample carrier operative for dry storage of a biological sample comprising polynucleotides, proteins, or a combination thereof,
        wherein the reception opening of said container is configured to receive said sample carrier, wherein the ejection opening of said container is configured to allow ejection of said sample carrier, and wherein said sample carrier is contained in said container and comprises an archived biological sample;
    inserting said ejector through the reception opening of said container;
    engaging said sample carrier contained in said container with said ejector; and
    ejecting said sample carrier from said container through said ejection opening.

2. The method of claim 1, wherein said storage system comprises a plurality of containers and wherein said method further comprises identifying a location of a target container in said storage system.

3. The method of claim 1, wherein said identifying and said aligning further comprise utilizing a signal received from a transceiver co-located with said sample carrier.

4. The method of claim 3, wherein said transceiver is activated by radio frequency energy.

5. The method of claim 3, wherein said transceiver is activated by optical energy.

6. The method of claim 1, wherein said inserting comprises piercing a film sealing said reception opening.

7. The method of claim 1, wherein said ejecting comprises piercing a film sealing said ejection opening.

8. The method of claim 1, further comprising providing a daughter plate to receive said sample carrier responsive to said ejecting.

9. The method of claim 1, further comprising re-wetting said sample carrier.

10. The method of claim 9, wherein said re-wetting comprises adding water or a buffer.

11. An archive system comprising:
- a receptacle having a support surface;
- a plurality of storage systems, wherein said storage systems are arranged on said support surface and each of said storage systems comprises:
  - a container having a reception opening and an ejection opening,
  - a first film sealing the ejection opening of said container; and
  - a sample carrier operative for dry storage of a biological sample comprising polynucleotides, proteins, or a combination thereof,
  - wherein the reception opening of said container is configured to receive said sample carrier, wherein the ejection opening of said container is configured to allow ejection of said sample carrier, and wherein said sample carrier is contained in said container; and
- an ejector apparatus operative to:
  - align an ejector with said container in a selected one of said plurality of storage systems;
  - insert said ejector through said reception opening in said container;
  - engage said sample carrier contained in said container with said ejector; and
  - eject said sample carrier from said container through said ejection opening.

12. The archive system of claim 11, further comprising a handling apparatus operative to engage selected ones of said plurality of storage systems.

13. The archive system of claim 12, wherein the handling apparatus is further operative to identify a selected one of said plurality of storage systems.

14. The archive system of claim 13, wherein said identifying comprises reading a bar code.

15. The archive system of claim 11, wherein each of said plurality of storage systems is oriented on end on said support surface.

16. The archive system of claim 11, wherein said plurality of storage systems is arranged into one or more stacks on said support surface.

17. The archive system of claim 11, wherein said ejector apparatus is further operative to replace a portion of said ejector after ejection of said sample carrier.

18. The archive system of claim 11, wherein said ejector apparatus is further operative to replace said ejector after ejection of said sample carrier.

19. The archive system of claim 11, wherein said ejector includes a piercing tip and said ejector apparatus is further operative to replace said piercing tip.

20. The archive system of claim 11, wherein said ejector apparatus is further operative to replace said ejector from a plurality of pre-cut ejectors.

* * * * *